(12) United States Patent
Ranki et al.

(10) Patent No.: US 8,143,029 B2
(45) Date of Patent: Mar. 27, 2012

(54) METHODS AND MEANS RELATED TO DISEASES

(75) Inventors: Annamari Ranki, Helsinki (FI); Sonja Hahtola, Espoo (FI); Leena Karenko, Helsinki (FI); Soile Tuomela, Turku (FI); Riitta Lahesmaa, Turku (FI); Kai J. E Krohn, Salmentaka (FI)

(73) Assignee: Valipharma, London (GB)

( * ) Notice: Subject to any disclaimer, the term of this patent is extended or adjusted under 35 U.S.C. 154(b) by 324 days.

(21) Appl. No.: 12/086,712

(22) PCT Filed: Dec. 21, 2006

(86) PCT No.: PCT/FI2006/050577
§ 371 (c)(1),
(2), (4) Date: Jun. 16, 2009

(87) PCT Pub. No.: WO2007/071829
PCT Pub. Date: Jun. 28, 2007

(65) Prior Publication Data
US 2010/0035971 A1    Feb. 11, 2010

Related U.S. Application Data

(60) Provisional application No. 60/753,268, filed on Dec. 22, 2005.

(51) Int. Cl.
C12P 19/34 (2006.01)
C12Q 1/68 (2006.01)
C12M 1/34 (2006.01)

(52) U.S. Cl. .................... 435/91.2; 435/6.1; 435/287.1

(58) Field of Classification Search .................. 435/91.2, 435/6.1
See application file for complete search history.

(56) References Cited

U.S. PATENT DOCUMENTS

| | | | |
|---|---|---|---|
| 2001/0051344 A1* | 12/2001 | Shalon et al. | 435/6 |
| 2003/0104528 A1 | 6/2003 | Glimcher et al. | |
| 2003/0211510 A1 | 11/2003 | Henderson et al. | |
| 2004/0005563 A1 | 1/2004 | Mack et al. | |
| 2004/0137566 A1 | 7/2004 | Tedder | |
| 2004/0197782 A1 | 10/2004 | Elchmuller et al. | |
| 2005/0089895 A1 | 4/2005 | Cheung et al. | |

FOREIGN PATENT DOCUMENTS

| | | |
|---|---|---|
| JP | 8-173187 | 7/1996 |
| WO | 02/072032 | 9/2002 |
| WO | 03/066898 | 8/2003 |
| WO | 03/080853 | 10/2003 |
| WO | 2004/067778 | 8/2004 |
| WO | 2005/024043 | 3/2005 |

OTHER PUBLICATIONS

Hoshikawa Y. et al. Physiol Genomics 12: 209-219, 2003.*
Cobb J.P. et al. Crit Care Med 2002 vol. 30, No. 12, pp. 2711-2721.*
Cheung V.G. et al. Nature Genetics (Mar. 2003) vol. 33, pp. 422-425.*
Chen G. et al. Molecular & Cellular Proteomics 1.4 (2002) pp. 304-313.*
Patent Abstracts of Japan of JP 8-173187 dated Jul. 9, 1996.
Turman, M. A., et al. "Characterization of a Novel Gene (NKG7) on Human Chromosome 19 that is Expressed in Natural Killer Cells and T Cells." Human Immunology (1993) vol. 36, No. 1 pp. 34-40.
Bagot, M., et al. "Interleukin-7 receptor expression in cutaneous T-cell lymphomas." British Journal of Dermatology (1996) vol. 135, pp. 572-575.
Sweeney, E. B., et al. "Interelukin 7 (IL-7) Receptor-Specific Cell Killing by $DAB_{389}$ IL-7: A Novel Agent for the Elimination of IL-7 Receptor Positive Cells." Bioconjugate Chem. (1998) vol. 9, pp. 201-207.
Foss, F. M., et al. "Characterization of IL7 Receptor Antagonists in Leukemia Cells: Inhibition of Proliferation and Altered Signal Transductioln." Proc. of Amer. Assoc. For Cancer Research Annual Meeting (2001) vol. 42, p. 876 [Abstract No. 4698].
Ginaldi, L., et al. "Levels of Expression of CD52 in Normal and Leukemic B and T Cells: Correlation with In Vivo Therapeutic Responses to Campath-aH." Leukemia Research (1998) vol. 22, No. 2, pp. 185-191.
Dyer, M. J. S., et al. "Remission Induction in Patients with Lymphoid Malignancies Using Unconjugated Campath-1 Monoclonal Antibodies." Leukemia and Lymphoma (1990) vol. 2, pp. 179-193.
Kennedy, G. A., et al. "Treatment of patients with advanced mycosis fungoides and Sezary syndrome with alemtuzumab." European Journal of Haematology (2003) vol. 71 pp. 250-256.
Dearden, C. "Alemtuzumab in Peripheral T-Cell Malignancies." Cancer Biotherapy & Radiopharmaceuticals (2004) vol. 19, No. 4, pp. 391-398.

(Continued)

*Primary Examiner* — Stephen Kapushoc
(74) *Attorney, Agent, or Firm* — Ladas & Parry LLP

(57) ABSTRACT

The present invention relates to the fields of genetics and oncology and provides methods for detecting cutaneous T-cell lymphomas (CTCL) or susceptibility to CTCL. Specifically, the present invention relates to a novel method for the diagnosis and follow-up of CTCL or CTCL subtype, the method comprising determination of expression of one or more genes, gene fragments or gene products. The present invention further relates to a novel method of detecting the response to CTCL therapy, the method comprising determining expression of one or more genes or gene fragments or gene products in a biological sample. The present invention further relates to a novel method of developing or improving CTCL therapy or developing anti-CTCL medicament, the method comprising screening agents affecting one or several of the genes or gene products. The present invention further relates to a novel method of treating CTCL patients, the method comprising affecting one or several of the genes or gene products. The present invention further relates to a novel test kit, the kit comprising the necessary means for detecting one or more genes, gene fragments or gene products. The present invention also relates to a use of one or more genes, gene fragments or gene products for determination, diagnosis or follow-up of CTCL or CTCL subtype and for detection of the response to CTCL therapy. The present invention also relates to a use of one or more target molecules for CTCL therapy or for the preparation of a medicament for treating CTCL.

9 Claims, 16 Drawing Sheets

OTHER PUBLICATIONS

Harashima, A., et al. "Transcription factor expression in B-cell precursor-leukemia cell lines: preferential expression of T-bet." Leukemia Research (2005) vol. 29, pp. 841-848.

Kleinhans, M., et al. "Functional expression of the eotaxin receptor CCR3 in CD30+ cutaneous T-cell lymphoma." Blood (2003) vol. 101, No. 4, pp. 1487-1493.

Mori, N., et al. "Elevated Expression of CCL5/Rantes in Adult T-cell Leukemia Cells: Possible Transactivation of the CCL5 Gene by Human T-cell Leukemia Virus Type 1 Tax." Int. J. Cancer (2004) vol. 111, pp. 548-557.

Mahadevan, D., et al. "Transcript profiling in peripheral T-cell lymphoma, not otherwise specified, and diffuse large B-cell lymphoma identifies distinct tumor profile signatures." Molecular Cancer Therapeutics (2005) vol. 4, No. 12, pp. 1867-1879.

Borges, L., et al. "LIR9, an immunoglobulin-superfamily-activating receptor, is expressed as a transmembrane and as a secreted molecule." Blood (2003) vol. 101, No. 4, pp. 1484-1486.

Nikolova, M., et al. "Engagement of ILT2/CD85j in Sezary syndrome cells inhibits their CD3/TCR signaling." Blood (2002) vol. 100, No. 3, pp. 1019-1025.

Kari, L., et al. "Classification and Prediction of Survival in Patients with the Leukemic Phase of Cutaneous T Cell Lymphoma." Journal of Experimental Medicine (2003) vol. 197, No. 11, pp. 1477-1488.

Tracey, L., et al. "Mycosis fungoides shows concurrent deregulation of multiple genes involved in the TNF signaling pathway: an expression profile study." Blood (2003) vol. 102, No. 3 pp. 1042-1050.

van Doorn, R., et al. "Aberrant Expression of the Tyrosine Kinase Receptor EphA4 and the Transcription Factor Twist in Sezary Syndrome Identified by Gene Expression Analysis." Cancer Research (2004) vol. 64, pp. 5578-5586.

Mao, X., et al. "Amplification and overexpression of *JUNB* is associated with primary cutaneous T-cell lymphomas." Blood (2003) vol. 101, No. 4, pp. 1513-1519.

Hahtola, S., et al. "Th1 Response and Cytotoxicity Genes are Down-Regulated in Cutaneous T-Cell Lymphoma." Clinical Cancer Research (2006) vol. 12, No. 16, pp. 4812-4821.

Dorfman, D. M., et al. "Differential Expression of T-bet, a T-box Transcription Factor Required for Th1 T-Cell Development, in Peripheral T-Cell Lymphomas." American Journal of Clinical Pathology (2003) vol. 120, No. 6, pp. 866-873.

Appay, V., et al. "Rantes: a versatile and controversial chemokine." Immunology Trends (2001).

Bagot, M., et al. "Isolation of Tumor-Specific Cytotoxic CD4+ and CD4+CD8dim+ T-Cell Clones Infiltrating a Cutaneous T-Cell Lymphoma." Blood (1998) vol. 91, pp. 4331-4341.

Berger, C. L., et al. "Cutaneous T-cell lymphoma: malignant proliferation of T-regulatory cells." Blood (2005) vol. 105, pp. 1640-1647.

Boehncke, W. H., et al. "A majority of proliferating T cells in cutaneous malignant T cell lymphomas may lack the high affinity IL-2 receptor (CD25)." Archives of Dermatological Research (1993) vol. 285, pp. 127-130.

Cairns, C. M., et al. "Lymphotactin Expression by Engineered Myeloma Cells Drives Tumor Regression: Mediation by CD4+ and CD8+ T Cells and Neutrophils Expressing XCR1 Receptor[1]." The Journal of Immunology (2001) pp. 57-65.

Crawley, J. J., et al. "Identification of frequent cytogenetic aberrations in hepatocellular carcinoma using gene-expression microarray data." Genome Biology (2002) vol. 3, No. 12, pp. 1-8.

Demers, M., et al. "A Novel Function for Galectin-7: Promoting Tumorigenesis by Up-regulating MMP-9 Gene Expression." Cancer Research (2005) vol. 65, No. 12, pp. 5205-5210.

Diederichs, S., et al. "S100 Family Members and Trypsinogens are Predictors of Distant Metastasis and Survival in Early-Stage Non-Small Cell Lung Cancer." Cancer Research (2004) vol. 64, pp. 5564-5569.

Diehl, S., et al. "The two faces of IL-6 on Th1/Th2 differentiation." Molecular Immunology (2002) vol. 39, pp. 531-536.

Dohring, C., et al. "Alternatively sliced forms of human killer inhibitory receptors." Immunogenetics (1996) vol. 44, pp. 227-230.

Dummer, R., et al. "Sezary syndrome T-cell clones display T-helper 2 cytokines and express the accessory factor-1 (interferon-gamma receptor beta-chain)." Blood (1996) vol. 88, pp. 1383-1389.

Duvic, M., et al. "$DAB_{389}$ IL2 Diphtheria Fusion Toxin Produces Clinical Responses in Tumor Stage Cutaneous T Cell Lymphoma.:" American Journal of Hematology (1998) vol. 58, pp. 87-90.

Egeblad, M., et al. "New Functions for the Matrix Metalloproteinases in Cancer Progression." Nature Reviews / Cancer (2002) vol. 2, pp. 161-173.

Eisen, M. B., et al. "Cluster analysis and display of genome-wide expression patterns." Proc. Natl. Acad, Sci. USA (1998) vol. 95, pp. 14863-14868.

Foss, F., et al. "A phase-21 trial of bexarotene and denileukin diftitox in patients with relapsed or refractory cutaneous T-cell lymphoma." Blood (2005) vol. 106, No. 2, pp. 454-457.

French, L. E., et al. "Impaired CD40L signaling is a cause of defective IL-12 and TNF-{alpha} production in Sezary syndrome: circumvention by hexameric soluble CD40L." Blood (2005) vol. 105, No. 1, pp. 219-225.

Gardiner, C. M., et al. "Different NK Cell Surface Phenotypes Defined by the DX9 Antibody are due to KIR3DL1 Gene Polymorphism[1]." The Journal of Immunology (2001) pp. 2992-3001.

Hamalainen, H., et al. "Distinct gene expression profiles of human type 1 and type 2 T helper cells." Genome Biology (2001) vol. 2, No. 7, pp. 1-11.

Hamalainen, H. K., et al. "Identification and Validation of Endogenous Reference Genes for Expression Profiling of T Helper Cell Differentiation by Quantitative Real-Time RT-PCR[1]." Analytical Biochemistry (2001) 299, pp. 63-70.

Hammacher, A., et al. "Interleukin-6 is a potent inducer of S100P, which is up-regulated in androgen-refractory and metastatic prostate cancer." International Journal of Biochemistry & Cell Biology (2005) 37, pp. 442-450.

Hassel, J. C., et al. "Serological Immunomarkers in Cutaneous T Cell Lymphoma." Dermatology (2004) 209, pp. 296-300.

Jones, D., et al. "Degree of CD25 Expression in T-Cell Lymphoma is Dependent on Tissue Site: Implications for Targeted Therapy." Clinical Cancer Research (2004) vol. 10, pp. 5587-5594.

Karenko, L., et al. "Primary Cutaneous T-Cell Lymphomas Show a Deletion or Translocation Affecting NAV3, the Human UNC-53 Homologue." Cancer Research (2005) 65 (18) pp. 8101-8110.

Karenko, L., et al. "Chromosomal Abnormalities in Cutaneous T-Cell Lymphoma and in Its Premalignant Conditions as Detected by G-Banding and Interphase Cytogenetic Methods." The Journal of Investigative Dermatology (1997) vol. 108, No. 1, pp. 22-29.

Karenko, L., et al. "Chromosomally Clonal T Cells in the Skin, Blood, or Lymph Nodes of Two Sezary Syndrome Patients Express CD45RA, CD45RO, CDw150, and Interleukin-4, but no Interleukin-2 or Interferon-γ." J. of Investigative Dermatology (2001) vol. 116, No. 1, pp. 188-193.

Kashiwakura, J., et al. "Txk, a Nonreceptor Tyrosine Kinase of the Tec Family, is expressed in T Helper Type 1 Cells and Regulates Interferon γ Production in Human T Lymphocytes." J. Exp. Med. (1999) vol. 190, No. 8, pp. 1147-1154.

Kim, S., et al. "α-Synuclein, Parkinson's disease, and Alzheimer's disease." Parkinsonism & Related Disorders (2004) 10, pp. S10-S13.

Klein, G., et al. "The possible role of matrix metalloproteinase (MMP)-2 and MMP-9 in cancer, e.g. acute leukemia." Critical Reviews in Oncology/Hematology (2004) 50 , pp. 87-100.

Lee, S. S.,et al. "Cell cycle aberrations by α-synuclein over-expression and cyclin B immunoreactivity in Lewy bodies." Neurobiology of Aging (2003) 24, pp. 687-696.

Liang, Y., et al. "Identification of a CD20-, FceRIβ-, and HTm4-Related Gene Family: Sixteen New MS4A Family Members Expressed in Human and Mouse." Genomics (2001) 72, pp. 119-127.

Lord, G. M., et al."T-bet is required for optimal proinflammatory CD4+ T-cell trafficking." Blood (2005) vol. 106, No. 10, pp. 3432-3439.

Lund, R., et al. "Identification of genes involved in the initiation of human Th1 or Th2 cell commitment." European Journal of Immunology (2005) 35, pp. 3307-3319.

Mao, X., et al. "Molecular cytogenetic analysis of cutaneous T-cell lymphomas: identification of common genetic alterations in Sezary syndrome and mycosis fungoides." British Journal of Dermatology (2002) 147, pp. 464-475.

Marshall, E. "Getting the Noise Out of Gene Arrays." Science (2004) vol. 306, pp. 630-631.

Mousses, S., et al. "Clinical Validation of Candidate Genes Associated with Prostate Cancer Progression in the CWR22 Model System using Tissue Microarrays[1]." Cancer Research (2002) 62, pp. 1256-1260.

Nagai, S., et al. "Comprehensive gene expression profile of human activated $T_h1$- and $T_h2$-polarized cells." International Immunology (2001) vol. 13, No. 3, pp. 367-376.

Olsen, E., et al. "Pivotal Phase III Trial of Two Dose Levels of Denileukin .Diftitox for the Treatment of Cutaneous T-Cell Lymphoma." Journal of Clinical Oncology (2001) vol. 19, No. 2, pp. 376-388.

Overall, C. M., et al. "Strategies for MMP Inhibition in Cancer: Innovations for the Post-Trial Era." Nature Reviews / Cancer (2002) vol. 2, pp. 657-672.

Pollack, J. R., et al. "Microarray analysis reveals a major direct role of DNA copy number alteration in the transcriptional program of human breast tumors." PNAS (2002) vol. 99, No. 20, pp. 12963-12968.

Poszepczynska-Guigne, E., et al. "CD158k/KIR3DL2 is a New Phenotypic Marker of Sezary Cells: Relevance for the Diagnosis and Follow-up of Sezary Syndrome." The Journal of Investigative Dermatology (2004) 122, pp. 820-823.

Press, O. W., et al. "Monoclonal antibody 1F5 (anti-CD20) serotherapy of human B cell lymphomas." Blood (1987) 69, pp. 584-591.

Rogge, L., et al. "Transcript imaging of the development of human T helper cells using oligonucleotide arrays." Nature Genetics (2000) vol. 25, pp. 96-101.

Sato, N., et al. "Indentification of maspin and S100P as novel hypomethylation targets in pancreatic cancer using global gene expression profiling." Oncogene (2004) 23, pp. 1531-1538.

Sheibani, K., et al. "Distribution of Lymphocytes with Interleukin-2 Receptors (TAC Antigens) in Reactive Lymphoproliferative Processes, Hodgkin's Disease, and Non-Hodgkins's Lymphomas . . . . " AJP (1987) , vol. 127, No. 1, pp. 27-37.

Symth, G. K. "Linear Models and Empirical Bayes Methods for Assessing Differential Expression in Microarray." Statistical Application S in Genetics and Molecular Biology (2004) No. 1, Article 3, pp. 1-26.

Szabo, S. J., et al. "A Novel Transcription Factor, T-bet, Directs Th1 Lineage Commitment." Cell (2000) vol. 100, pp. 655-669.

Takeba, Y., et al. "Txk, a Member of Nonreceptor Tyrosine Kinase of Tec Family, Acts as a Th1 Cell-Specific Transcription Factor and Regulates IFN-$\gamma$ Gene Transcription[1]." The Journal of Immunology (2002) 168, pp. 2365-2370.

Tan, P. K., et al. "Evaluation of gene expression measurements from commercial microarray platforms." Nucleic Acids Research (2003) vol. 31, No. 19, pp. 5676-5684.

Uhrberg, M., et al., "Definition of gene content for nine common group B haplotypes of the Caucasoid population: KIR haplotypes contain between seven and eleven KIR genes." Immunogenetics (2002) 54, pp. 221-229.

Uhrberg, M., et al. "Human Diversity in Killer Cell Inhibitory Receptor Genes." Immunity (1997) vol. 7, pp. 753-763.

Vowels, B. R., et al. "Aberrant Cytokine Production by Sezary Syndrome Patients: Cytokine Secretion Pattern Resembles Murine Th2 Cells." The Journal of Investigative Dermatology (1992) vol. 99, No. 1, pp. 90-94.

Vowels, B. R., et al. "Th2 Cytokine mRNA Expression in Skin in Cutaneous T-Cell Lymphoma." The Journal of Investigative Dermatology (1994) vol. 103, No. 5, pp. 669-673.

West, A. B., et al. "To die or grow: Parkinson's disease and cancer." Trends in Neurosciences (2005) vol. 28, No. 7, pp. 348-352.

Willemze, R., et al. "WHO-EORTC classification for cutaneous lymphomas." Blood (2005) vol. 105, No. 10, pp. 3768-3785.

Willemze, R., et al. "EORTC Classification for Primary Cutaneous Lymphomas: A Proposal from the Cutaneous Lymphoma Study Group of the European Organization for Research and Treatment of Cancer." Blood (1997) vol. 90, No. 1, pp. 354-371.

Wu, Z., et al. "A Model-Based Background Adjustment for Oligonucleotide Expression Arrays." Journal of the American Statistical Association (2004) vol. 99, No. 468, pp. 909-917.

Kaltoft, K., et al. "Cytogenetic Findings in Cell Lines from Cutaneous T-Cell Lymphoma." Dermatologic Clinics (1994) vol. 12, No. 2, pp. 295-304.

Sakata, K., et al. "Expression of Matrix Metalloproteinases-2 and -9 by Cells Isolated from the Peritoneal Fluid of Women with Ovarian Carcinoma." Acta Cytologica (2002) vol. 46, No. 4, pp. 697-703.

Wood, G. S., et al. "Mycosis fungoides skin lesions contain CD8+ tumor-infiltrating lymphocytes expressing an activated, MHC-restricted cytotoxic T-lymphocyte phenotype." Journal of Cutaneous Pathology (1994) pp. 151-156.

Duvic, M. "Bexarotene and $DAB_{389}$ IL-2 (Denileukin Diftitox, ONTAK) in treatment of Cutaneous T-Cell Lymphomas: Algorithms." Clinical Lymphoma (2000) vol. 1, Supp. 1, pp. S51-S55.

Guerreiro Da Silva, I. D. C., et al. "S100Pcalciuk-biding protein overexpression is associated with immmortalization of human breast epithelial cells in vitro and early stages of breast cancer development in vivo." Int'l J. of Oncology (2000) 16, pp. 231-240.

Ishibashi, K., et al. "Identification of a new multigene four-transmembrane family (MS4A) related CD20, HTm4 and $\beta$ subunit of the high-affinity IgE receptor."

Chaitidis, P., et al. "Gene expression alterations of human peripheral blood monocytes induced by medium-term treatment with the TH2-cytokines interleukin-4 and -13." *Cytokine* (2005) vol. 30, No. 6, pp. 366-377.

Laszlo, K., et al. "Classification and Prediction of Survival in Patients with the Leukemic Phase of Cutaneous T Cell Lymphoma." Journal of Experimental Medicine (2003) vol. 197, No. 11, pp. 1477-1488.

Lorraine Tracey, et al. "Mycosis fungoides shows concurrent deregulation of multiple genes involved in the TNF signaling pathway: an expression profile study." Blood (2003) vol. 102, No. 3 pp. 1042-1050.

Ishibashi, K., et al. "Identification of a new multigene four-transmembrane fmaily (MS4A) related CD20, HTm4 and $\beta$ subunit of the high-affinity IgE receptor", Gene (Feb. 7, 2001) vol. 264, issue 1, pp. 87.93.

* cited by examiner

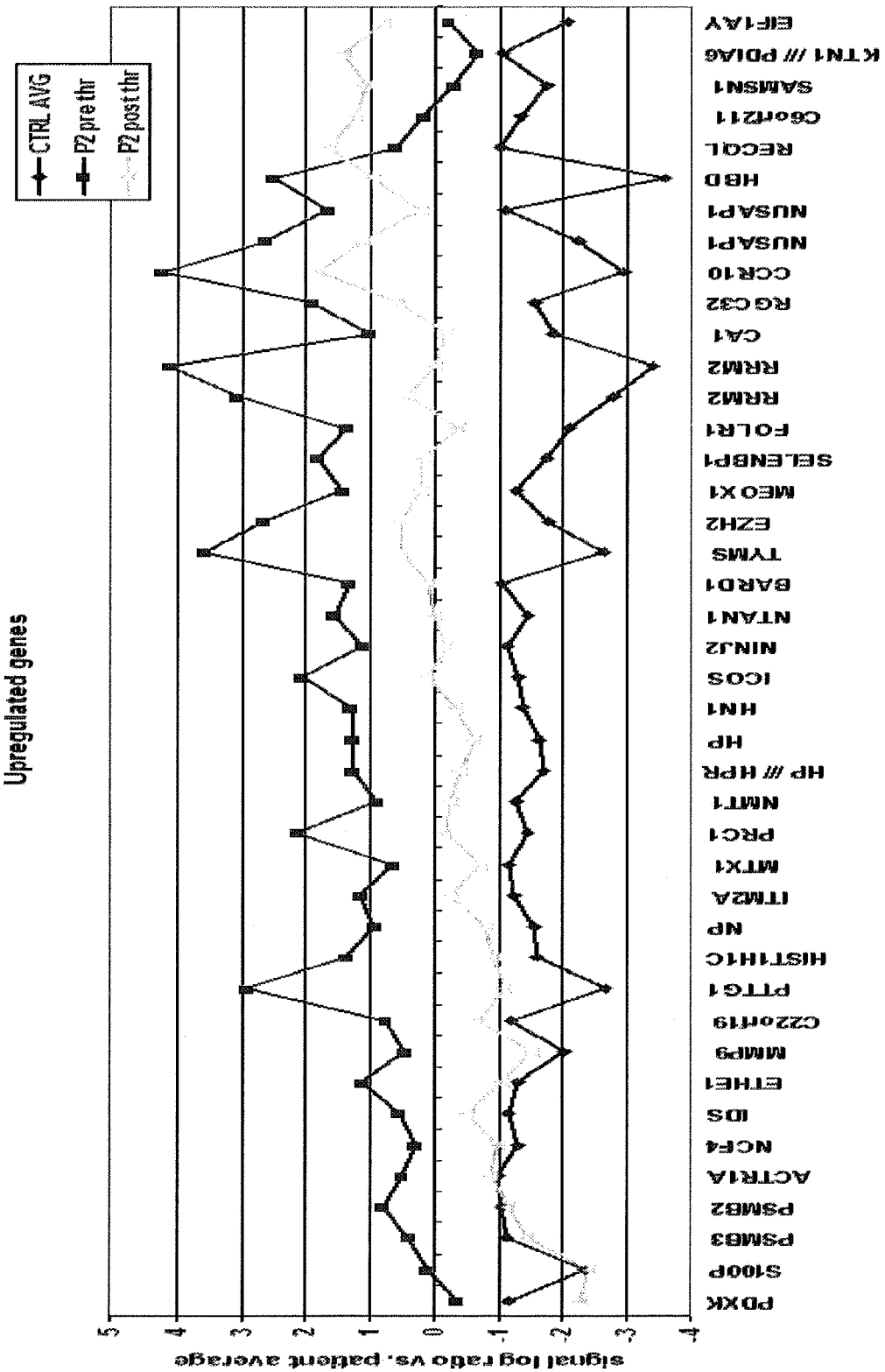

METHODS AND MEANS RELATED TO DISEASES

CROSS-REFERENCE TO RELATED APPLICATIONS

This application is a 371 National Phase Entry Application of co-pending International Application PCT/FI2006/050577, filed 21 Dec. 2006, which designated the U.S. and which claims the benefit under 35 U.S.C. §119(e) of U.S. Provisional Application 60/753,268, filed 22 Dec. 2005.

FIELD OF THE INVENTION

The present invention relates to the fields of genetics and oncology and provides methods for detecting cutaneous T-cell lymphomas (CTCL) or susceptibility to CTCL. Specifically, the present invention relates to a novel method for the diagnosis and follow-up of CTCL or CTCL subtype, the method comprising determination of expression of one or more genes, gene fragments or gene products. The present invention further relates to a novel method of detecting the response to CTCL therapy, the method comprising determining expression of one or more genes or gene fragments or gene products in a biological sample. The present invention further relates to a novel method of developing or improving CTCL therapy or developing anti-CTCL medicament, the method comprising screening agents affecting one or several of the genes or gene products. The present invention further relates to a novel method of treating CTCL patients, the method comprising affecting one or several of the genes or gene products. The present invention further relates to a novel test kit, the kit comprising the necessary means for detecting one or more genes, gene fragments or gene products. The present invention also relates to a use of one or more genes, gene fragments or gene products for determination, diagnosis or follow-up of CTCL or CTCL subtype and for detection of the response to CTCL therapy. The present invention also relates to a use of one or more target molecules for CTCL therapy or for the preparation of a medicament for treating CTCL.

BACKGROUND OF THE INVENTION

Primary cutaneous T-cell lymphomas (CTCL) represent a group of malignancies of mature T lymphocytes, which show a homing preference for skin. CTCL most often occurs in people aged between 40 and 60 and the two major clinical variants of CTCL are mycosis fungoides (MF) or Sezary syndrome (SzS).

Mycosis fungoides (MF), the most common type of CTCL, presents with skin lesions showing epidermotrophic clonal T lymphocytes (Willemze R et al. Blood 90:354-371, 1997). CTCL may also present in a leukaemic form with erythrodermic skin involvement and lymphadenopathy (Sezary syndrome, SzS), and 10-20% of MF cases transform to large T-cell lymphoma with time (Willemze R et al. Blood 90:354-371, 1997, Willemze R et al. Blood 105:3768-3785, 2005). Ten-year relative survival of MF, the most benign form of the cutaneous T-cell lymphomas ranges from 100% to 41%, depending on the degree of skin involvement. Patients with SzS have a prognosis with an estimated 5-year survival of 15% (Willemze R et al. Blood 90: 354-71, 1997). Therefore, many patients with advanced disease do not respond to therapy and furthermore, many patients having some response to therapy will later suffer a relapse. Thus, there is an urgent need for life-saving therapeutics.

The molecular mechanisms leading to CTCL are still largely unknown. Previously performed microarray studies have found no uniform gene expression signatures (Kari L et al. J Exp Med 197:1477-1488, 2003, van Doorn R et al. Cancer Res 64:5578-5586, 2004, Tracey L et al. Blood 102: 1042-1050, 2003), most likely due to a wide range of different experimental designs and microarray platforms used. On one hand, an expression profile suggesting upregulation of genes involved in TNF signaling pathway was found among MF skin samples (Tracey L et al. Blood 102:1042-1050, 2003). On the other hand, among SzS samples, many Th2-specific transcription factors (like Gata-3 and JunB) were found overexpressed, while underexpressed genes included CD26, Stat4, and IL-1 receptors in one study (Kari L et al. J Exp Med 197:1477-1488, 2003) and decreased expression of some tumor suppressor genes such as TGF-$\beta$ receptor 11 with overexpression of EphA4 and Twist in an other study (van Doorn R et al. Cancer Res 64:5578-5586, 2004). Due to the different probe and sample sets, and to the lack of publicly available raw data of array hybridizations, comparison of the published data is difficult. Recently, the very low concordance in array profiles obtained with the same samples on different devices has been clearly demonstrated (Tan P K et al. Nucleic Acids Res 31:5676-5684, 2003, Marshall E. Science 306:630-631, 2004). To get a better comprehension of CTCL pathogenesis, we analyzed fresh cells from various tissues of both SzS and MF, and compared their expression profiles with DNA copy number data, since DNA copy number changes contribute to variation in gene expression (Pollack J R et al. Proc Natl Acad Sci USA 99:12963-12968, 2002).

Helper T (Th) cells are essential for developing an immune response by activating antigen-specific effector cells and recruiting cells of the innate immune system such as macrophages and mast cells. Th1 commitment relies on the local production of IL-12, and Th2 development is promoted by IL-4 in the absence of IL-12. Th1 cells participate in cell-mediated immunity and control intracellular pathogens. The cytokines produced by Th1 cells stimulate phagocytosis and destruction of microbial pathogens. Th2 cells are essential for antibody-mediated immunity by stimulating the production of antibodies. Thus, Th2 cells participate in controlling extracellular pathogens. Excessive Th1 responses are involved in many autoimmune diseases, whereas excessive Th2 responses are known to lead for example to chronic diseases, including allergies, asthma, and chronic bronchitis. Increased Th2 cytokine levels have also been revealed in various malignancies including CTCL (Kari L et al. J Exp Med 197:1477-1488, 2003).

Profound understanding of CTCL improves the possibilities of diagnosing or curing the disease. None of the previous documents describes CTCL specific genes or gene products presented in this patent application (Kari L et al. J Exp Med 197:1477-1488, 2003, van Doorn R et al. Cancer Res 64:5578-5586, 2004, Tracey L et al. Blood 102:1042-1050, 2003, and US2005074761). Therefore, this invention provides novel tools for CTCL diagnostics and therapeutics.

BRIEF DESCRIPTION OF THE INVENTION

An object of the present invention is to provide novel solutions for the above problems.

Thus, a group of novel genes has been shown to associate with CTCL or susceptibility to CTCL.

The object of the invention is to provide novel methods and means for detecting CTCL or susceptibility to CTCL, such methods and means allowing an early diagnosis of the disease.

Another object of the invention is to provide novel methods and means for the prediction, diagnosis and follow-up of CTCL or CTCL subtype, such methods and means being specific and reliable and allowing identification as early as possible.

Yet another object of the invention is to provide novel methods and means for detecting the response to CTCL therapy, such methods and means allowing selection of specific and effective treatment for a patient.

Still another object of the invention is to provide novel biomarkers useful in detection of CTCL or potential for developing CTCL.

Still another object of the invention is to provide novel biomarkers useful in diagnosing CTCL or CTCL subtype as well as following up CTCL or CTCL subtype.

Still another object of the invention is to provide novel biomarkers useful in detecting the response to therapy of CTCL.

Still another object of the invention is to introduce new possibilities for combating the disease and for the recovery of the patient by providing novel biomarkers useful as target molecules for therapies or prevention of CTCL.

Still another object of the invention is to provide a diagnostic kit for detecting novel CTCL associated genes, gene fragments or gene products.

Yet another object of the invention is to provide novel methods and means for developing or improving CTCL therapy.

Still another object of the invention is to provide novel methods and means for developing anti-CTCL medicament.

Yet another object of the invention is to provide novel methods and means for treating CTCL.

The present invention relates to a novel method for detection of CTCL or susceptibility to CTCL, characterized by determining expression of one or more genes, gene fragments or gene products selected from the group comprising or consisting of S4A4A, NKG7, IL7R, CD52, TBX21, SCYA5, and LIR9 in a biological sample, whereby under- or overexpression of one or more of said genes, gene fragments or gene products indicates CTCL or susceptibility to CTCL.

The present invention relates to a novel method for detection of CTCL or susceptibility to CTCL, characterized by determining expression of MS4A4A, NKG7, IL7R, CD52, TBX21, SCYA5, and LIR9 genes, gene fragments or gene products in a biological sample, whereby under- or overexpression of one or more of said genes or gene products indicates CTCL or susceptibility to CTCL.

The present invention further relates to a novel method for the diagnosis and follow-up of CTCL or CTCL subtype, characterized by determining expression of one or more genes, gene fragments or gene products selected from the group comprising MS4A4A, NKG7, IL7R, CD52, TBX21, SCYA5, and LIR9 in a biological sample, whereby under- or overexpression of one or more of said genes, gene fragments or gene products indicates CTCL or susceptibility to CTCL or CTCL subtype.

The present invention further relates to a novel method of detecting the response to CTCL therapy, characterized by determining expression of one or more genes, gene fragments or gene products selected from the group comprising MS4A4A, NKG7, IL7R, CD52, TBX21, SCYA5, and LIR9, in a biological sample, whereby normalization of under- or overexpression of one or more of said genes, gene fragments or gene products indicates response of CTCL therapy.

The present invention further relates to a novel diagnostic kit, characterized by comprising the necessary means for detecting one or more genes, gene fragments or gene products selected from the group comprising MS4A4A, NKG7, IL7R, CD52, TBX21, SCYA5, and LIR9.

The present invention further relates to uses of one or more genes, gene fragments or gene products selected from the group comprising MS4A4A, NKG7, IL7R, CD52, TBX21, SCYA5, and LIR9 for determining CTCL, for the diagnosis and follow-up of CTCL or CTCL subtype, and for detecting the response to therapy of CTCL.

The present invention further relates to a use of one or more genes, gene fragments or gene products selected from the group comprising MS4A4A, NKG7, IL7R, CD52, TBX21, SCYA5 and LIR9 as target molecules for CTCL therapy.

The present invention also relates to a method for developing or improving CTCL therapy, the method comprising screening of agents affecting one or several of the genes or gene products selected from the group comprising MS4A4A, NKG7, IL7R, CD52, TBX21, SCYA5, and LIR9, whereby an agent having said effect allows developments and improvements of CTCL therapy.

The present invention also relates to a method for developing anti-CTCL medicament, the method comprising screening of agents affecting one or several of the genes or gene products thereof selected from the group comprising MS4A4A, NKG7, IL7R, CD52, TBX21, SCYA5, and LIR9, whereby an agent having said effect is tested as a medicament.

The present invention also relates to a method for treating CTCL patients, characterized by affecting one or several of the genes or gene products selected from the group comprising MS4A4A, NKG7, IL7R, CD52, TBX21, SCYA5, and LIR9.

BRIEF DESCRIPTION OF THE DRAWINGS

In the following the invention will be described in greater detail by means of preferred embodiments with reference to the attached drawings, in which.

DETAILED DESCRIPTION OF THE INVENTION

Figure 1A:
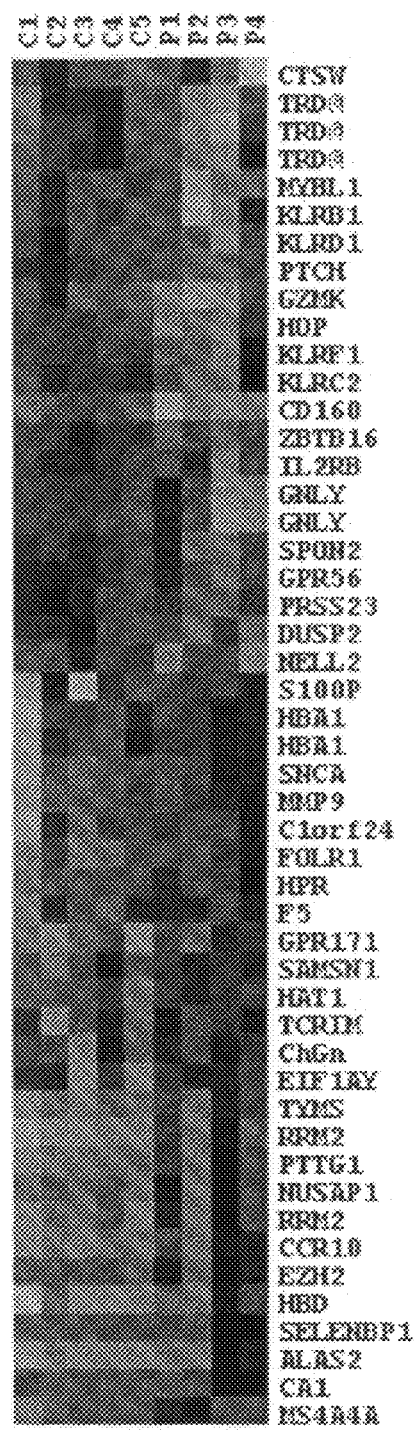
FIG. 1 shows substantial differences that were observed in gene expression profiles in SzS PBMC, MF CD4+ and skin biopsy samples, compared to corresponding control samples. The most differentially ($p<0.05$ and fold change>3) expressed genes between patient and control samples are shown: SzS PBMC (A), MF skin biopsies (B), MF CD4+ cells (C) and MF PBMC (D). The expression of the genes selected for further analysis from each category is displayed: SzS PBMC (E), MF skin biopsies (F), MF CD4+ cells (G) and MF PBMC (H). In Figures: P=patients, C=controls, red=upregulated (brightest red=fold change value 3), green=downregulated (brightest green=fold change value−3).

Novel targets for CTCL or CTCL subtype diagnosis as well as for prevention, amelioration and therapy have been revealed.

Aberrant regulation of one or several genes or gene products, specifically MS4A4A, NKG7 (also known as GIG1), IL7R (also known as IL7R-ALPHA or CD127), CD52, TBX21 (also known as TBET), SCYA5 (also known as CCL5 or TCP228), and LIR9 (also known as ILT11 or CD85F), is associated with CTCL. The genes have been described in the prior art.

The present invention is based on a method of detecting CTCL or susceptibility to CTCL by determining differential regulation of one or more genes or gene products selected from the group comprising MS4A4A, NKG7, IL7R, CD52, TBX21, SCYA5, and LIR9.

Specifically, CTCL or CTCL subtype is mycosis fungoides (MF) or Sezary syndrome (SzS).

In one specific embodiment of the method of the invention over- or underexpression of one or several of the genes is characteristic of Th1 or Th2 polarization.

In one specific embodiment of the method of the invention over-expression of LIR9 is characteristic of Th2 polarization.

In one specific embodiment of the method of the invention under-expression of NKG7, TBX21 or SCYA5 is characteristic of Th2 polarization.

In one specific embodiment of the method of the invention under- or overexpression indicates the early stage of CTCL.

In one specific embodiment of the method of the invention under- or overexpression indicates the late stage of CTCL.

In one specific embodiment of the method of the invention expression of genes, gene fragments or gene products that is one or several genes, gene fragments or gene products listed in Tables 2 or 3, is determined.

The present invention is also based on a diagnostic kit comprising the necessary means for detecting one or more genes, gene fragments or gene products selected from the group comprising MS4A4A, NKG7, IL7R, CD52, TBX21, SCYA5, and LIR9.

In one specific embodiment of the kit of the invention the test kit comprises the necessary means for detecting genes MS4A4A, NKG7, IL7R, CD52, TBX21, SCYA5, and LIR9 or gene fragments or gene products thereof.

As used herein the expression "gene product" refers to a mRNA, protein or to any product achieved directly or indirectly from the gene.

As used herein the expression "gene fragment" refers to any part of a gene or an incomplete or isolated portion of a gene, which is detectable in the methods of the invention.

As used herein the expressions "over- and underexpression" refer to up- or down-regulation of a gene or gene products, correspondingly.

As used herein the expression "biological sample" refers to any suitable tissue sample, such as whole blood or biopsy from the tissue or lymph node. The biological sample can be, if necessary, pretreated in a suitable manner known to those skilled in the art.

As used herein the expression "subtype" refers to a restricted type of disease, functional disorder or defect such as mycosis fungoides or Sezary syndrome.

As used herein the expression "Th1 or Th2 polarization" refers to a path, where pre-Th cells begin to proliferate, become activated, and depending on the stimulation gain characteristics of Th1 or Th2 cells and develop to Th1 or Th2 cells.

As used herein the expression "by screening agents" refers to any in vitro or in vivo method known by the man skilled in the art, which method can be used in evaluating or measuring the effect of an agent on genes or gene products.

As used herein the expression "necessary means for detecting genes, gene fragments or gene products" refers for example to any markers, probes, primers, antibodies as well as standards, labels, buffers, diluents, and washing solutions suitable for detection. The expression also refers to compositions or diagnostic kits, which are provided for example in the form of an ELISA, protein chip, nucleic acid chip or a membrane loaded with DNA, RNA or protein, or any other composition known by the man skilled in the art. Optionally, diagnostic kits comprise instructions to carry out the methods for detecting genes, gene fragments or gene products.

In the present invention, information on the poorly understood pathogenesis of CTCL was obtained by microarray gene expression analysis with Affymetrix oligonucleotide array containing over 22 000 transcripts and by combining the data with results obtained with CGH. Real-time quantitative PCR and immunohistochemistry were used to validate the microarray data.

Th1-specific genes such as SCYA5, NKG7, and TBX21 were found to be downregulated in SzS samples (FIG. 1E) and genes e.g. LIR9 and MS4A4A were found upregulated in both MF and SzS samples (Table 3). In lesional MF skin samples IL7R and CD52 were upregulated. Chromosomal arms 1q, 3p, 3q, 4q, 12q, 16p and 16q revealed amplified chromosomal areas and overexpressed genes. Chromosomal areas 4q and 12q also contain down-regulated genes and deleted areas.

After successful therapy of one SzS patient a group of 57 probe sets was changed towards the control PBMC phenotype. The therapy-responsive genes included e.g. S100P, CCR10, BCL2, VAV3 and GZMB.

Differential regulation of genes, gene fragments or gene products can be caused by various events or mechanisms such as point mutations, polymorphisms, translocations, genetic or chromosomal deletions, insertions, gene or chromosomal amplifications, gene conversions and any other defects. Silencing of genes or chromosomal areas can be caused for example by epigenetic mechanisms such as methylation.

According to the method of the present invention, expression of genes, gene fragments, and gene products can be detected in a biological sample by any known suitable detection method. These methods comprise detecting a gene expression or methods based on detecting the copy number of the gene, DNA or chromosome and/or those based on detecting the gene expression products (mRNA or protein). Such methods are easily recognized by those skilled in the art and include for example enzymatic methods, electrophoretic methods or physical methods such as conventional polymerase chain reaction (PCR)-methods, RT-PCR, real time quantitative PCR, single strand conformation polymorphism (SSCP), heteroduplex analysis, fragment analysis, DNA sequencing, minisequencing, primer extension methods, microarrays, mass spectrometry and denaturing high performance liquid chromatography (DHPLC). In addition, suitable methods include conventional G-banding techniques, comparative genomic hybridization (CGH), in situ hybridisations, such as FISH, mRNA in situ hybridization, Northern analysis, and Southern as well as Western analyses, immunohistochemistry, and other immunoassays, such as ELISA. Epigenetic assays such as methylation assays may also be used.

Any markers suitable for detecting differential gene regulation, include any biological markers such as microsatellite markers, SNP-markers, any probes, primers or antibodies associated with genes or gene products.

The current finding of up- and downregulation of specific genes can be used in the field of CTCL diagnostics. Diagnostic tests, based on the current findings, may also have implications in the tests for screening patients for eventual subclinical forms of CTCL. Such screening tests may be based on the detection of secretory proteins upregulated in CTCL. Furthermore, any diagnostic test developed on basis of the currently revealed genetic alterations in CTCL may be used to monitor or predict the disease outcome, to predict the drug responsiveness of the patients and in clinical follow-up.

The current finding of up- and downregulation of specific genes in CTCL can also be used in the field of therapy, when restoration of the normal function of genes can be used. This may be reached by enhancing the expression of functionally homologous genes, by introducing an intact gene or by using an altered form of the gene or antisense oligonucleotide or small inhibitory RNA against the gene or gene product in any technique presently available for gene therapy to prevent the progression of a proliferating disease. Such techniques include the in vivo, ex vivo and in situ therapy methods comprising transducing or transfecting an intact or altered gene (or its functional domains) in a recombinant or peptide form or as antisense oligonucleotides or in an expression vector to the patient or inserting the altered gene or oligonucleotide into a carrier, which is then introduced into the patient. It is noteworthy that the delivery of those genes, which are hoped to be expressed in a therapeutic manner can be achieved by epicutaneous delivery of naked DNA vectors expressing the gene of interest. One possible way to express a therapeutic gene would be to use viral vectors, especially ones with a preferential homing to skin and dermis. Alternatively, monoclonal or humanized antibodies, modified antibodies or peptides binding to the protein or to the fusion gene generated can be used to suppress the function of the altered protein. Antibodies against the protein could also be used to carry and target other agents, such as cytotoxic substances, to specific cells. In particular, a transient or a permanent cure of CTCL may be achieved by above-mentioned methods.

Observed genetic changes as well as consequent alteration in the expression profile in CTCL and SzS are useful to design novel drugs for these malignancies. Such drugs may be monoclonal antibodies targeted against membrane proteins that are expressed on the malignant cells or against secretory proteins that in turn affect the host regulatory processed, such as immune response against the malignant cells. Furthermore, monoclonal antibodies or other response modifiers may be targeted against secretory products of the malignant cells that favor the spread of the tumor. An important group of target molecules for therapeutic approaches for CTCL are the genes and gene products involved in immune regulation.

To identify shared expression profile to the most common forms of CTCL and to mask the effect of reactive T-cells, likely to influence the results, our sample material consisted of several cell subpopulations of both SzS and MF patients. Despite the difference in the quantity of malignant T-cells in SzS and MF blood, we identified a common gene expression pattern. Our findings provide basis for previous findings of a preferential Th2 type cytokine profile in SzS, since we identified a panel of Th1-specific genes (Szabo S J et al. Cell 100:655-669, 2000, Hamalainen H et al. Genome Biol 2:RESEARCH0022, 2001, Rogge L et al. Nat Genet 25:96-101, 2000, Lund R et al. Eur J Immunol 35:3307-3319, 2005, Nagai S et al. Int Immunol 13:367-376, 2001, and Kashiwakura J et al. J Exp Med 190:1147-1154, 1999), e.g. TBX21, SCYA5, NKG7, XCL1, TXK, and GZMB, to be down-regulated in SzS samples.

Of the Th1-specific genes downregulated in SzS, TBX21 and TXK represent transcription factors essential for Th commitment to Th1 phenotype. They both regulate IFNγ expression, the expression of which we have previously shown to be absent from the chromosomally clonal, i.e. true malignant cells in SzS (Karenko L et al. J Invest Dermatol 116:188-193, 2001). Also, they belong to a positive feedback loop promoting Th1 cytokine secretion leading to Th1 development (Szabo S J et al. Cell 100:655-669, 2000, Takeba Y et al. J Immunol 168:2365-2370, 2002). The expression of TBX21 was very low also in one MF patient, but the overall variation among MF patients, representing various stages, was greater than among the leukaemic SzS patients. Recently, TBX21 has also been shown to regulate the CD4+ cell trafficking to inflammatory sites, by regulating e.g. the expression of the chemokine ligand CXCR3 (Lord G et al. Blood 106:3432-3439, 2005), but TBX21 has not been linked to CTCL before. Our finding of TBX21 downregulation in SzS thus explains the previous observation of the loss of CXCR3 expression along the progression of MF (Appay V and Rowland-Jones SL. Trends Immunol 22:83-87, 2001). Furthermore, the expression of SCYA5 (RANTES), a chemokine mediating the trafficking and homing of T-cells (Turman M A et al. Hum Immunol 36:34-40, 1993), and that of NKG7 (Vowels B R et al. J Invest Dermatol 99:90-94, 1992) was downregulated in our SzS PBMC samples. These genes have also been linked to Th cell differentiation, and they are more abundantly expressed in cells polarized to Th1 than to Th2 direction (Hamalainen H et al. Genome Biol 2:RESEARCH0022, 2001, Rogge L et al. Nat Genet 25:96-101, 2000, Lund R et al. Eur J Immunol 35:3307-3319, 2005, Nagai S et al. Int Immunol 13:367-376, 2001).

Other genes, which were upregulated during the early polarization of T-helper cells into Th2-direction (Lund R et al. Eur J Immunol 35:3307-3319, 2005) and were upregulated in both our SzS and MF PBMC samples, included the SLOOP gene. S100P has a role in cell cycle progression and differentiation, and its upregulation has been found in various malignancies (Vowels B R et al. J Invest Dermatol 103:669-673, 1994, Dummer R et al. Blood 88:1383-1389, 1996, Cairns C M et al. J Immunol 167:57-65, 2001, and Dohring C et al. Immunogenetics 44:227-230, 1996). Since an expression bias for S100P was found in MF blood samples, too, S100P may have a role in the early oncogenesis of CTCL. Also, we found membrane-bound LIR9 (215838_at) to be overexpressed in SzS PBMC, MF PBMC and MF CD4+ samples compared to controls. LIR9 is a member of leukocyte immunoglobulin-like receptor family mostly expressed on monocytes and neutrophils but not on normal T cells. In monocytes, activation of LIR9 has been shown to induce calcium mobilization and secretion of IL-1β, TNF-α and IL-6 (Gardiner C M et al. J Immunol 166:2992-3001, 2001). Of the latter, dysregulation of TNF signalling pathway has been linked to both SzS and MF pathogenesis (Tracey L et al. Blood 102: 1042-1050, 2003 and Guerreiro Da Silva I D et al. Int J Oncol 16:231-240, 2000), and IL-6 has been shown to be a marker of SzS tumor burden and to correlate with clinical stage in non-leukemic CTCL (Sato N et al. Oncogene 23:1531-1538, 2004). IL-6 is an important cytokine for Th2 cell differentiation (Hammacher A et al. Int J Biochem Cell Biol 37:442-450, 2005), but also induces S100P (Cairns C M et al. J Immunol 167:57-65, 2001).

Taking together the above knowledge (Table 3), our findings seem to explain the occurrence of a functional bias towards Th2 in Sezary syndrome (Mousses S et al. Cancer Res 62:1256-1260, 2002, Diederichs S et al. Cancer Res 64:5564-5569, 2004, and Sheibani K et al. Am J Pathol 127: 27-37, 1987). Our findings also indicate that a bias towards Th2 takes place already in the MF stage, prior to progression to the leukaemic phase. Such a skewing is likely to influence the progressive immune dysregulation in CTCL and would thus provide a growth advantage for the malignant cell clone(s).

Of the cytotoxicity-associated genes, we found downregulation of XCL1 (lymphotactin), previously shown to augment antitumor responses (Boehncke W H. Arch Dermatol Res 285:127-130, 1993), and GZMB (granzymeB). We have previously shown, with the combination of immunihisto-chemistry and FISH, that granzymeB is absent from the clonal cells in skin and lymph node samples of SzS (Karenko L et al. J Invest Dermatol 116:188-193, 2001). KIR3DL2, a member of the killer cell immunoglobulin-like receptors, has previously been suggested as a phenotypic marker for Sezary cells (Poszepczynska-Guigne E et al. J Invest Dermatol 122:820-823, 2004) and has been found upregulated in SzS (van Doorn R et al. Cancer Res 64:5578-5586, 2004). Contradictory, we found KIR3DL2 gene to be downregulated in SzS. However, the LIR9 gene, located in the same leukocyte receptor cluster as KIR3DL2 was overexpressed. This discrepancy of observations may be due to the considerable polymorphism of the KIR3DL2 gene (Jones D et al. Clin Cancer Res 10:5587-5594, 2004, Duvic M et al. Am J Hematol 58:87-90, 1998). Thus, our data provide evidence for the downregulation of several cytotoxicity-associated genes in SzS.

We found IL2Rβ to be downregulated in SzS blood samples, which is of interest since IL2 is the major cytokine for T-cell activation and proliferation. IL2R consists of three subunits, of which IL2Rβ and IL2Rγ are expressed on resting T-cells and upregulated by e.g. IL-2. Previously, the high/intermediate affinity IL2R (α/p55/CD25+β/p75/CD122+γ/p64/CD132 chains/β+γ chains) has been reported to be expressed on about 50% of CTCL cells (Olsen E et al. J Clin Oncol 19:376-388, 2001, Duvic M. Algorithms. Clin Lymphoma 1 Suppl 1:S51-5, 2000, and Foss F et al. Blood 106: 454-457, 2005). Consequently, IL2-targeted therapy has been used for CTCL, most recently with a fusion protein denileukin diftitox (ONTAK) (Borges L et al. Blood 101:1484-1486, 2003). Interestingly, the retinoid X receptor (RXR) retinoid, bexarotene, a new therapeutic agent for MF (French L E et al. Blood 105:219-225, 2005), has been shown to upregulate both the p55 and p75 subunits of IL-2R. This upregulation, in turn, enhances the susceptibility of the malignant cells to denileukin diftitox, resulting in overall response rates of 67% in relapsed CTCL patients (Hassel J C et al. Dermatology 209:296-300, 2004).

We also observed, for instance, that one member of the MS4A superfamily (Liang Y and Tedder T F. Genomics 72:119-27, 2001), MS4A4A was upregulated on SzS cells. Another member of this superfamily, CD20, is already now the target of monoclonal antibody mediated therapy in large B-cell lymphomas (Press O W et al. Blood 69:584-91, 1987). We therefore propose, that the MS4A4A is useful as a target molecule for therapy of SzS.

Another potential target membrane protein is LIR9 (215838_at) found to be over expressed on SzS. Similarly to MS4A4A, specific monoclonal antibodies against LIR9 (215838_at), preferentially humanized or hybrid forms, are useful as a therapeutic principle. However, several other potential forms of drug acting on membrane proteins can be designed, based on the findings in this patent application, such forms being for example aptomeres or agonistic peptides. Furthermore, genetically altered natural ligands for the membrane protein that inhibits or strengthens the action of the natural ligand may be used as a therapeutic principle.

Another potential target molecule for therapeutic approaches is the S100P gene, which has a role in cell cycle progression and differentiation. Its upregulation has been found in various malignancies (Vowels B R et al. J Invest Dermatol 103:669-673, 1994, Dummer R et al. Blood 88:1383-1389, 1996, Cairns C M et al. J Immunol 167:57-65, 2001, and Dohring C et al. Immunogenetics 44:227-230, 1996) and its expression is regulated by steroid hormones, notably by androgens and progestins. We propose therefore that similar principles are useful for therapy of CTCL.

Several expression alterations of the invention tended to skew the Th1/Th2 balance. Furthermore, genes that would be involved in the activation of cytotoxic T-cells (CTL) were down regulated. Although it is not clear how a chance in the immunological profile of the T-cells in CTCL will lead to malignancy, it is noteworthy that the effective therapy with bexarotene and ONTAK leads to a Th1 favoured balance. Therefore, it can be assumed that any therapeutic principle leading to the same but involving those genes and gene products noticed in the current work can be employed.

In addition to the genes involved in immune regulation, two genes, commonly upregulated in our samples, were of interest. The SNCA gene, mapping to chromosome 4q21, was upregulated in all studied tissue or cell types of MF and SzS patients. Amplifications of 4q are frequent in CTCL (Diehl S and Rincon M. Mol Immunol 39:531-536, 2002) and in our integrated analysis, 4q turned out to be one of the areas with overexpressed genes and DNA copy number amplifications. SNCA is a major component of protein aggregates present in Parkinson's disease (Mao X et al. Br J Dermatol 147:464-475, 2002). Although some genes linked to Parkinson's disease may also have aberrant expression levels in cancers (Kim S et al. Parkinsonism Relat Disord 10 Suppl 1:S9-13, 2004), such a connection has not been found for SNCA so far. However, overexpression of SNCA has been shown to cause increased cell proliferation (West A B et al. Trends Neurosci 28:348-352, 2005). The matrix metalloproteinase MMP-9 was overexpressed in SzS and MF PBMC samples. This provides new aspects for the pathogenesis of CTCL since MMPs, in addition to their role in facilitating tumor cell invasion and metastasis (Lee S S et al. Neurobiol Aging 24:687-696, 2003 and Klein G et al. Crit Rev Oncol Hematol 50:87-100, 2004), are involved in cancer initiation, possibly by activating intracellular mediators that are inducers of genomic damage and may cause genomic instability (Overall C M and Lopez-Otin C. Nat Rev Cancer 2:657-672, 2002, Demers M et al. Cancer Res 65:5205-5210, 2005, and Sakata K et al. Acta Cytol 46:697-703, 2002). Concordant to our finding, MMP-9 overexpression has been previously observed in MF in relation to an advancing stage (Egeblad M and Werb Z. Nat Rev Cancer 2:161-174, 2002). Thus, our observation suggests that the role of MMPs should be studied further at the early stages of CTCL carcinogenesis.

Previously, several studies on CTCL have pointed out chromosomal instability as a hallmark of the disease. In SzS samples, we observed down-regulation of VAV3, which has structural similarities with the NAV3 gene, frequently deleted in CTCL (Karenko L et al. Cancer Res 65:8101-8110, 2005). The DLG5 tumor suppressor gene (Karenko L et al. J Invest Dermatol 108:22-29, 1997), also downregulated in SzS samples, is located in 10q23, a chromosomal area often deleted in CTCL (Diehl S and Rincon M. Mol Immunol 39:531-536, 2002 and Kaltoft K et al. Dermatol Clin 12:295-304, 1994). In this study, we have for the first time correlated the chromosomal changes with aberrations observed in gene expression level in the same patient subset. We identified seven chromosome arms, namely 1q, 3p, 3q, 4q, 12q, 16p and 16q, where both gene expression and DNA copy number was changed to the same direction. All these arms contain overexpressed genes and amplified chromosomal areas in our data set. Areas 4q and 12q also contain down-regulated genes and deleted areas. Previously, it has been shown with breast cancer samples by using array CGH, that a 2-fold change in DNA copy number is associated with an analogous 1.5-fold change in mRNA expression and at least 12% of the differences seen at transcription level were due to the variation in gene copy number (Pollack J R et al. Proc Natl Acad Sci USA 99:12963-12968, 2002).

In summary, detection of differential regulation of genes or gene products during CTCL initiation and progression will contribute to early diagnosis of disease and treatment of patients. The present invention discloses for the first time the role of at least one or several of the genes MS4A4A, NKG7, IL7R, CD52, TBX21, SCYA5, and LIR9 in CTCL. The present invention also discloses that detection of up- or down-regulation of these genes or gene products allows identification of CTCL patients or patients with an increased risk to develop CTCL. Discoveries of novel diagnostics and follow-up methods reveal new possibilities in the field of CTCL medicine.

The following examples are given for further illustration of the invention.

It will be obvious to a person skilled in the art that, as the technology advances, the inventive concept can be implemented in various ways. The invention and its embodiments are not limited to the examples described above but may vary within the scope of the claims.

Example 1

Genes expressed differentially among CTCL patients and Controls a) Patient and Control Samples Altogether, 30 samples obtained from 18 patients volunteering to the study were analyzed (Table 1). Peripheral blood mononuclear cell (PBMC) samples were obtained from 12 Sezary syndrome and mycosis fungoides patients and lesional skin biopsies from 9 mycosis fungoides patients (stage IA-IVB; defined according to the WHO-European Organization for Research and Treatment of Cancer classification for cutaneous lymphomas; Willemze R et al. Blood 105:3768-3785, 2005). More precisely, Affymetrix (Santa Clara, Calif.) analysis was done for 6 PBMC or CD4+-enriched cell samples of four Sezary syndrome patients and for 11 PBMC, CD4+, or skin lesion samples of five mycosis fungoides patients (Table 1). The percentage of Sezary cells (medium-sized lymphoid cell with a highly cleaved "cerebriform" nucleus and darkly clumped chromatin) among peripheral blood lymphocytes of Sezary syndrome patients ranged from 16% to 70%. None of the Sezary syndrome patients had received any anticancer therapy before sampling. Real-time quantitative PCR (qPCR) analysis was done for PBMC samples of six Sezary syndrome patients and for 12 PBMC, CD4+, or lesional skin samples of seven mycosis fungoides patients. In addition, skin lesion samples of two Sezary syndrome and seven mycosis fungoides patients were studied immunohistologically (Table 1). For reference material, blood samples were obtained from 5 healthy volunteers and skin biopsies were obtained from 10 voluntary patients with nonmalignant, lymphoid skin infiltrates (Table 1). The study was approved by the Ethical Re-view Board of the Skin and allergy hospital, Helsinki University Hospital.

b) RNA Isolation

Peripheral blood mononuclear cells (PBMC) from patients and healthy controls were collected by Ficoll Paque density gradient centrifugation (Ficoll-Paque PLUS, Amersham Biosciences, Uppsala Sweden), and CD4 positive cells were enriched with magnetic beads (CD4+ T-cell isolation kit #130-053-101, or CD4+ MicroBeads #130-045-101, Miltenyi Biotec, Bergisch Gladbach, Germany). Total RNA was isolated with Trizol Reagent (Invitrogen, Life Technologies, Grand Island, N.Y.). Fresh skin biopsies were immediately placed in RNA Later buffer (Ambion, Austin, Tex.), and RNA was collected by homogenizing the tissue in Trizol Reagent, whereafter RNA isolation was performed with Qiagen RNeasy kit according to manufacturer's instructions.

c) Analysis of Gene Expression Microarray Data 100 ng of purified (RNeasy Mini, Qiagen, Valencia, Calif.) RNA was prepared for hybridization according to Affymetrix small sample protocol (Affymetrix Technical note, GeneChip® Eucaryotic Small Sample Target Labelling Assay Version II). cDNA was hybridized against Affymetrix HG-U133A chip (Affymetrix, Santa Clara, Calif.). Gene expression estimates were calculated using the GC-RMA procedure (Wu Z et al. Journal of the American Statistical Association 99:909-917, 2004). In each two-group comparison, the statistical significance of the difference in gene expression levels between the groups was assessed with a modified t-test (Smyth GK. Statistical Applications in Genetics and Molecular Biology 3:Article 3, 2004). A gene was considered changed if the p-value of the test was less than 0.05 and there was at least a 2-fold change in the mean expression levels. The statistical analyses were carried out with R (cran.r-project.org) packages Affy and Limma and visualization with the TreeView software (Eisen M B et al. Proc Natl Acad Sci USA 95:14863-14868, 1998).

d) Identification of Regional Biases in Gene Expression

Patient-specific gene expression profiles were constructed by calculating gene expression ratios between each patient and the average of the matched controls. To assess regional biases in the expression profiles, the microarray probe sets were mapped along the chromosomes using the Bio-conductor annotation package hgu133a. To determine whether the set of expression ratios that map to a particular chromosomal arm exhibit upward or downward bias, a sign test was applied (Crawley J J and Furge K A. Genome Biol 3:RESEARCH0075, 2002). The algorithm scores a gene as up- or down-regulated if the expression change is at least 1.8-fold, and the sign test determines whether the corresponding chromosomal arm contains a statistically significant number of genes that change in the same relative direction. An expression bias was considered significant if the p-value of the sign test was less than 0.05. Of the acrocentric chromosomes only q-arms were included in the analysis.

e) Genes Expressed Differentially Among CTCL Patients and Controls

Figure 1B:
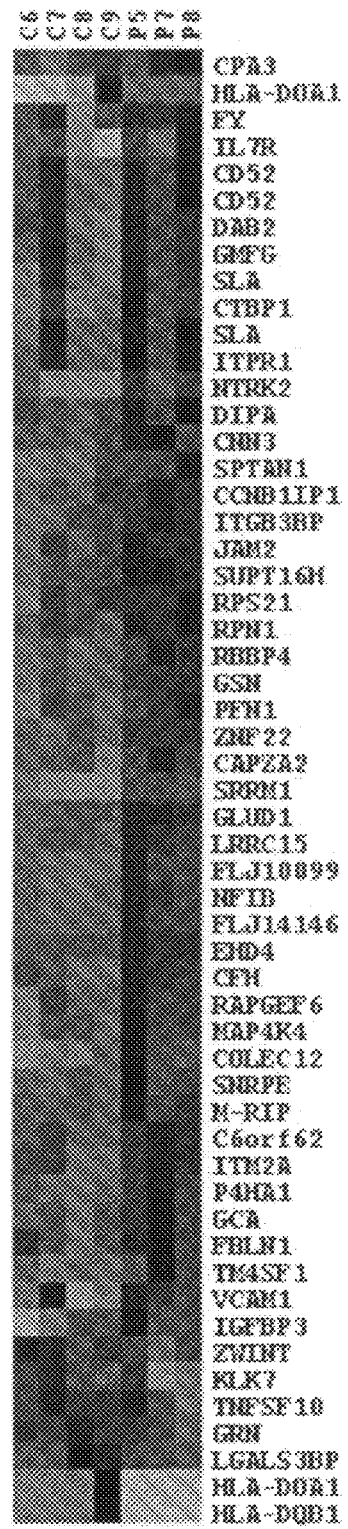
Figure 1C:
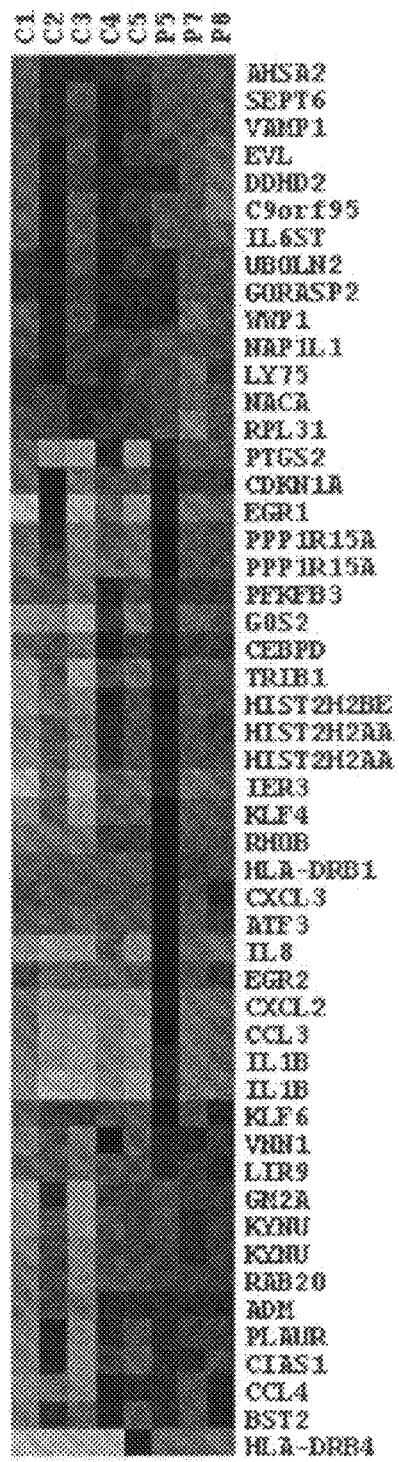
Figure 1D:
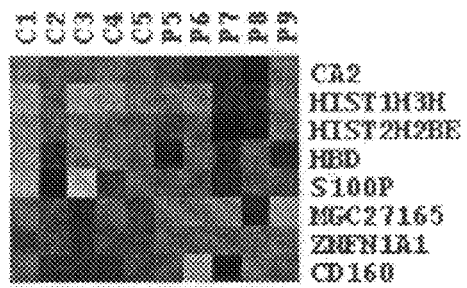

We identified altogether 168 probe sets (fold change>2, p-value<0.05) to be differentially regulated in SzS PBMC samples compared to control PBMC samples (FIG. 1A; FIG. 1 shows differentially regulated genes in all studied cell populations with fold change exceeding the value 3) and substantial variation of gene expression between control and MF skin samples (FIG. 1B). Since the number of malignant cells in SzS patient blood samples is considerably greater than that in MF patient blood samples, the gene expression profiles varied remarkably between SzS and MF PBMC samples (FIG. 2A). However, a subset of genes was found to change in a similar manner both in SzS and MF PBMC samples (FIG. 2B). To mask the effect of reactive or regulatory T-cells, commonly present in the samples of CTCL (Wood G S et al. J Cutan Pathol 21(2):151-156, 1994, Bagot M et al. Blood 91:43314341, 1998, and Berger C L et al. Blood 105:1640-1647, 2005), comparison of microarray data from different cell populations was performed, and changes common to different cell sources of MF patients (PBMC, CD4+ lymphocytes, lesional skin) as well as for SzS PBMC samples were identified (Table 2).

Figure 1E:
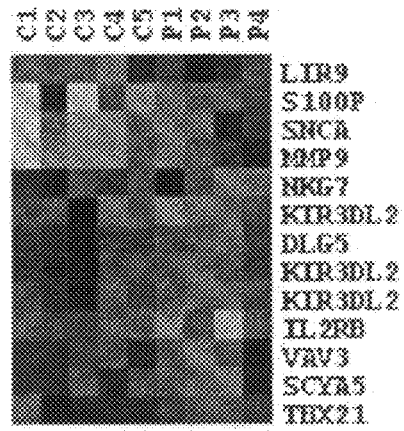
Figure 1F:
Figure 1G:
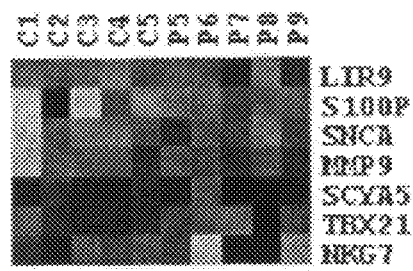
Figure 1H:
Figure 2A:
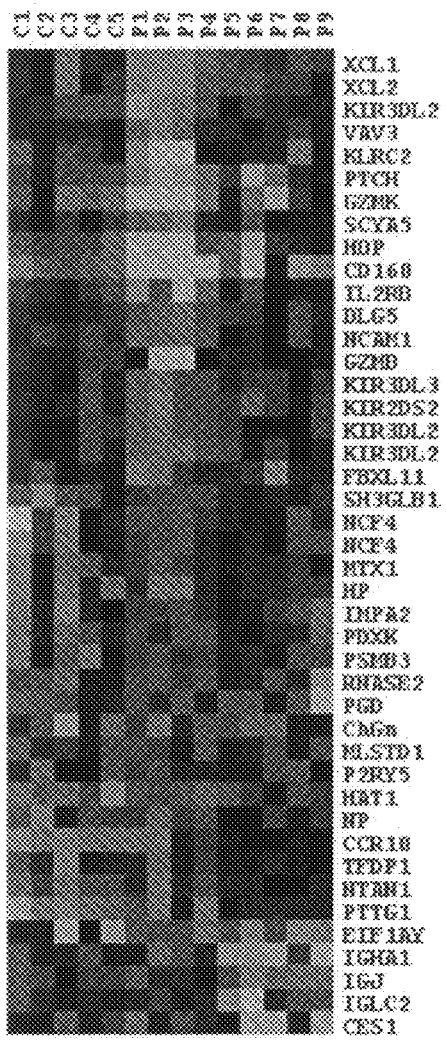
FIG. 2A shows genes distinguishing between Sezary syndrome (P1-4) and mycosis fungoides (P5-9). The analysis was performed by comparing the Sezary syndrome and mycosis fungoides PBMC samples together and selecting the genes distinguishing these two subtypes. The genes that were also differentially regulated between control samples and either Sezary syndrome or mycosis fungoides samples were included in the final data.
Figure 2B:
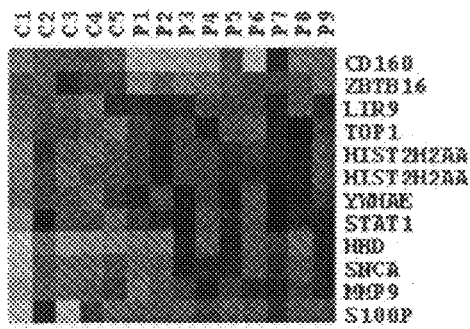
FIG. 2B shows a subset of genes found to change in a similar manner both in SzS (P1-4) and MF (P5-9) PBMC samples when compared to controls (C1-5).

Two Th1-specific genes (SCYA5 and NKG7), and IL-2Rβ, VAV3, DLG5, and KIR3DL2 were found to be over 2-fold downregulated in SzS samples (FIG. 1E). Genes upregulated in both MF and SzS blood samples included e.g. S100P and MMP-9. In lesional MF skin samples, compared to inflammatory dermatoses, IL7R and CD52 were upregulated. SNCA and LIR9 genes were upregulated in several cell populations of SzS and MF patients (Table 2). In addition, TBX21 was selected for further analysis based on its crucial role in Th1 differentiation.

Example 2

Real-Time Quantitative PCR and Immunohistochemistry

The key findings of gene expression data were confirmed with real-time quantitative PCR (qPCR). RNA samples were treated with Deoxyribonuclease 1, Amplification grade (Invitrogen Life Technologies, Carlsbad, Calif.) to eliminate possible genomic DNA and the purity of RNA was checked with RT run. The cDNA was prepared with Superscript II kit (Gibco BRL, Life Technologies, Paisley, Scotland). TBX21, NKG7, SCYA5, SLOOP, and house keeping gene EF1α were run with FAM (reporter) and TAMRA (quencher) duallabeled probes and other genes with ProbeLibrary probes (Exiqon A/S, Vedbaek, Denmark). Primer and probe sequences are listed in table 4. Linearity of amplification was confirmed by running standard curves for each amplicon and specificity of the reagents was verified by gel electrophoresis. The PCR reactions were carried out using ABsolute QPCR ROX mix (ABgene, Epsom, UK) with 300 nM primers and 200 nM probe. Detection was done with Applied Bio-systems's ABI Prism 7700 sequence detector (15 min 95° C. followed by 40 cycles of 15 s 95° C. and 1 min 60° C.). The results were normalized against EF1a detection value (Hamalainen HK et al. Anal Biochem. 299: 63-70, 2001).

Immunostainings for CD52 (Abcam, Cambridge, UK, diluted in 1:100), IL7R (R&D Systems, MN, USA, 1:10), IL7 (R&D Systems, 1:20), and KLK10 (R&D Systems, 1:30) were performed with Vectastain Elite Mouse kit (Vector Laboratories, Burlingame, Calif.), according to manufacturer's instructions. The immunostainings were carried out on frozen tissue sections of four CTCL patients included in the Affymetrix study, of 5 additional CTCL patients, and of 5 controls with eczema or lichen planus. MMP9 immunostaining was performed on formalin fixed paraffin embedded tissue sections of six CTCL patients included in the Affymetrix study and on controls with lichen planus and psoriasis using a mouse monoclonal antihuman MMP9 antibody (Research Diagnostics Inc, Flanders, N.J.; diluted in 1:50) as previously described by Saarialho-Kere and coworkers 1993.

Figure 3A:
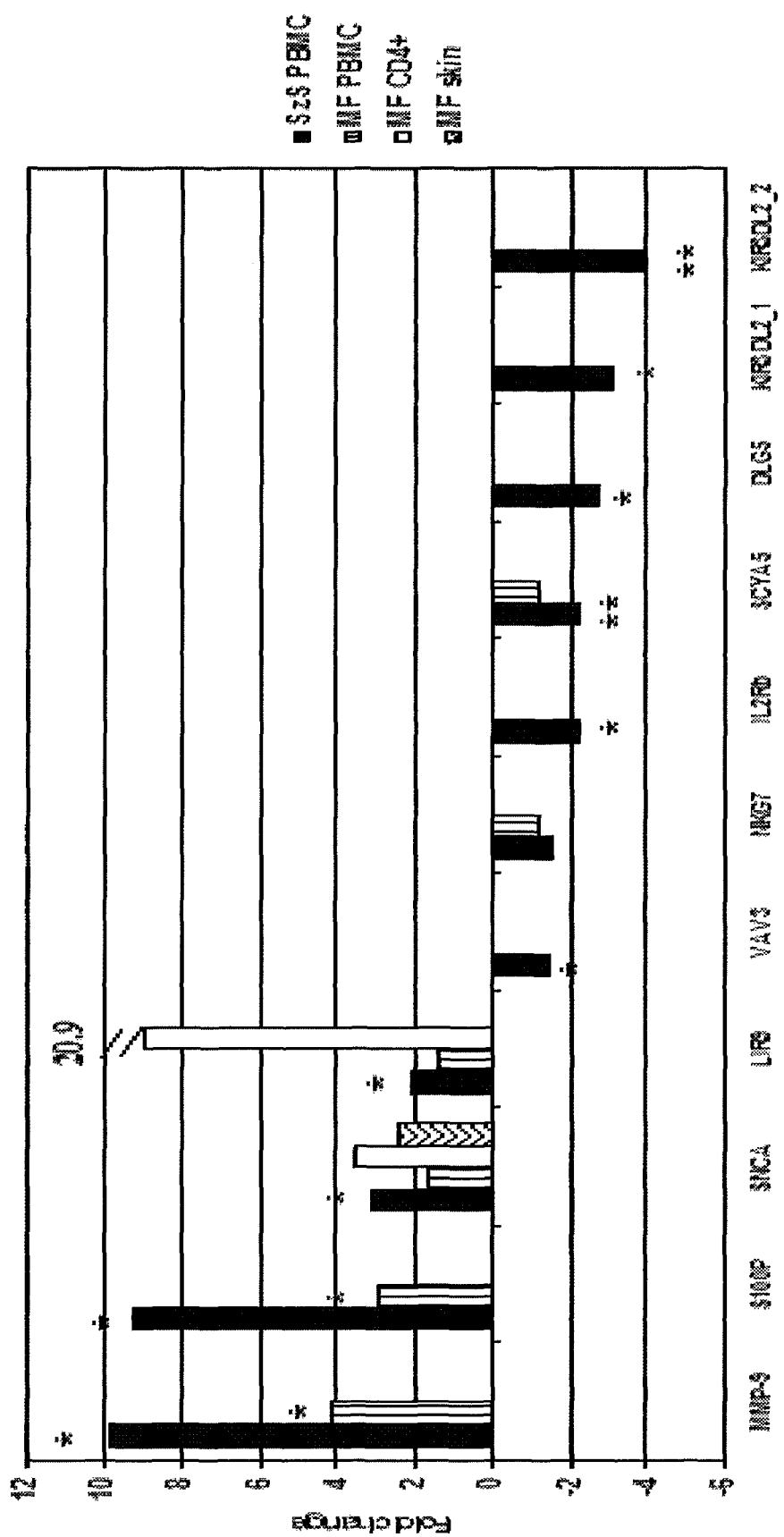
FIG. 3A shows quantitative PCR, performed on 10 genes.
Figure 3B:
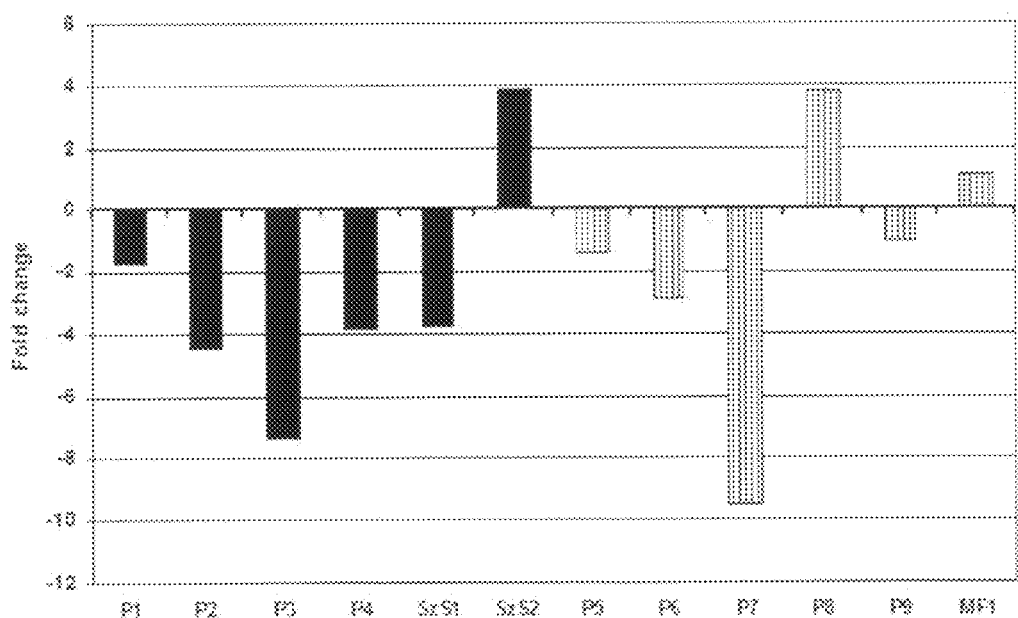
FIG. 3B shows the downregulation of TBX21 gene in PBMC samples of both SzS (P1-4 and SzS1-2) and MF patients (P5-9 and MF1).

Quantitative PCR, performed on 10 genes (FIG. 3), and immunohistochemistry, performed on four gene products (CD52, IL7R, IL7, MMP-9), validated the microarray data (FIGS. 6A-D). Especially, we wanted to make sure that our array results on KIR3DL2, previously reported to be a marker gene of CTCL (Poszepczynska-Guigne E et al. J Invest Dermatol 122:820-823, 2004), and now found downregulated in our SzS patients, were not due to differences in target sequence. Therefore, the KIR3DL2 result was confirmed by using qPCR reagents detecting the same sequence as the Affymetrix probe set (207314_x_at) and region previously reported (Uhrberg M et al. Immuno-genetics 54:221-229, 2002). Both sets of reagents for KIR3DL2 inevitably showed that the expression of this gene was downregulated in our sample set. Interestingly, we also show the downregulation of TBX21 (T-bet) gene in PBMC samples of both SzS and MF patients (FIG. 3B). Downregulation in the expression of SCYA5 (RANTES), and NKG7 were observed also in MF PBMC samples (FIG. 3A).

In immunohistochemistry (FIG. 6), CD52 protein was expressed by the majority (in average, 3 of 4) of skin-infiltrating lymphocytes of all CTCL patients when compared with inflammatory dermatoses with sparse expression. IL7R was expressed in basal keratinocytes (focally) but also in skin-infiltrating lymphocytes of all CTCL biopsies. The number of lymphocytes or keratinocytes expressing IL7R was, in average, thrice higher than in control samples. No difference in the expression levels of IL7 protein was found between CTCL patients and controls. MMP-9 protein was demonstrable in 25% to 50% of infiltrating lymphocytes in Sezary syndrome samples, whereas MMP-9 expression in mycosis fungoides samples was variable. In inflammatory dermatoses, the lymphocytes did not express MMP-9.

Example 3

Chromosomal regions showing both gene expression and Gene Copy Number Changes a) Comparative Genomic Hybridization (CGH) and Multifluor Fluorescent In Situ Hybridization (mFISH)

CGH was performed as previously reported (Karenko L et al. J Invest Dermatol 112:392-395, 1999) from the DNA of three SzS and three MF patients (Table 1). Nine to twelve metaphases were included in the analysis for each case. As an internal control, normal male and female DNA were cohybridized and only differences in sex chromosomes were identified. MFISH of metaphase preparations from cases 1-3, 5, 7, and 8, was performed as described previously (Karenko L et al. Cancer Res 65:8101-8110, 2005). At least 50 metaphases were analyzed for each case.

Figure 4A:
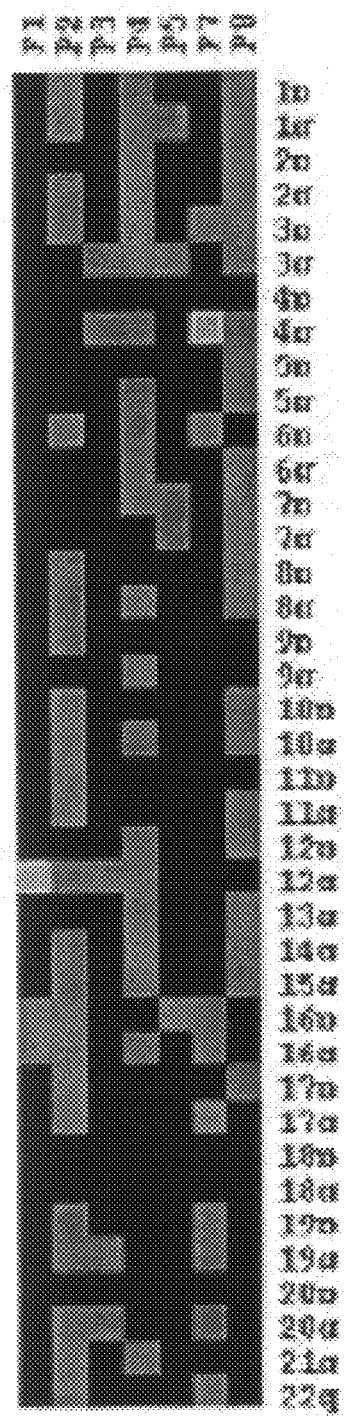
FIG. 4A shows gene expression profiles by chromosome arms in four SzS PBMC (patients P1-4) and three MF skin samples (patients P5, P7, P8).
Figure 4B:
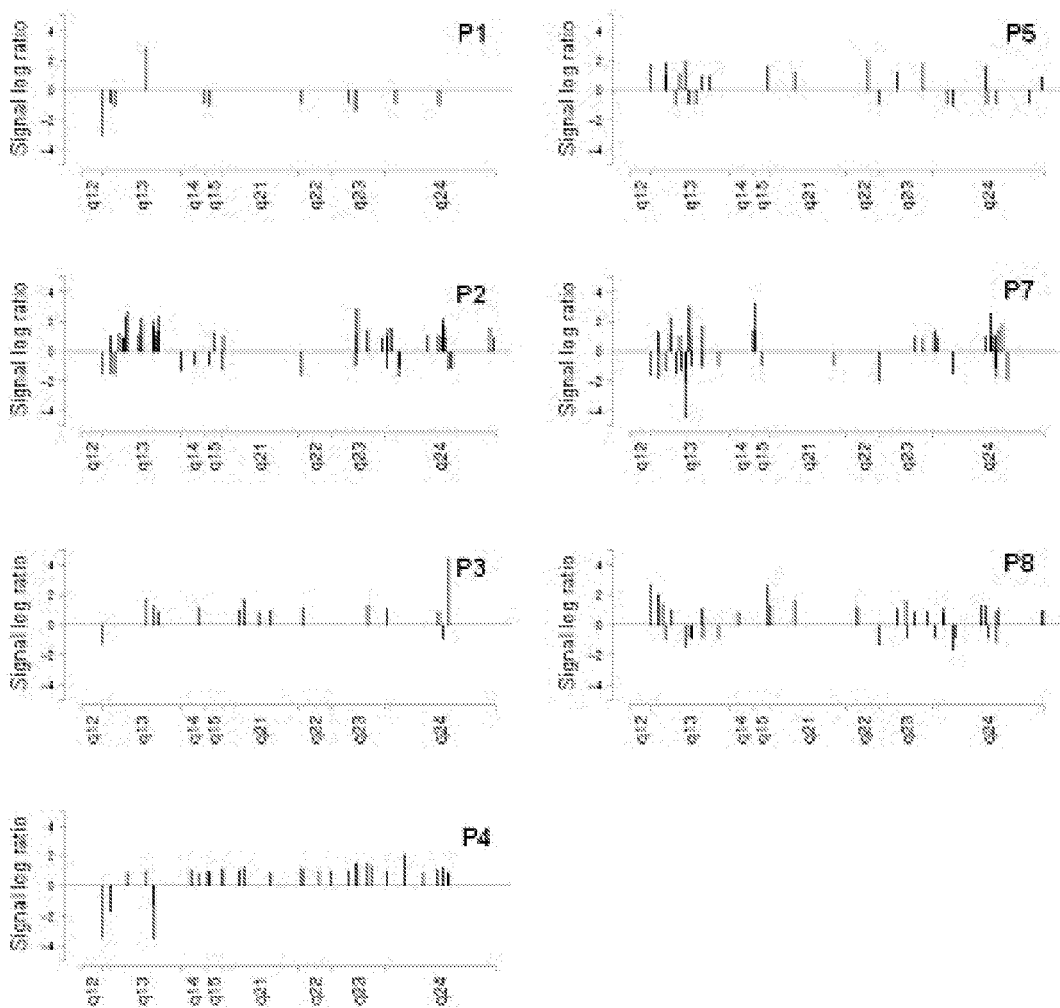
FIG. 4B shows gene expression ratios of Szs PBMC and MF PBMC mapped to chromosome 12q.

Finally, we examined the gene expression profiles by chromosome arms in four SzS PBMC and three MF skin samples. Five chromosomal arms showed consistently significant upward bias in gene expression in at least four of the seven patients: 1q, 3p, 3q, 16p, and 16q. Also, in chromosomes 4q and 12q, both an upward and a downward bias was detected (FIG. 4A). As an example, FIG. 4B illustrates the gene expression ratios mapped to chromosome 12q. Clusters of differentially expressed genes can be visualized especially in the areas 12q13 and 12q23-q24.

Figure 4C:
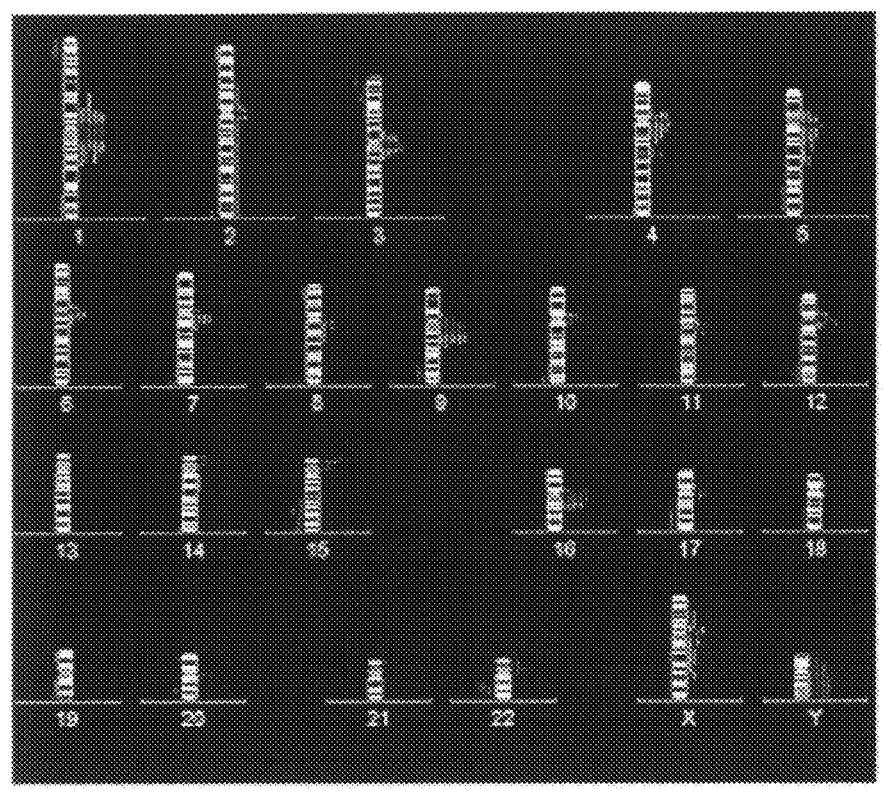
FIG. 4C shows combined CGH profiles of three Sezary syndrome (blood samples) and three mycosis fungoides (skin samples) patients.

To integrate the chromosomal and transcriptomic data, the chromosomal regions identified with the sign test were compared to the chromosomal aberrations detected by CGH. In three of the identified seven chromosomal arms, 1q, 4q, and 16q, a significant gain was detected also by the CGH analysis in at least four of the MF skin and SzS blood samples. For example, the SNCA gene found to be upregulated locates to cytoband 4q21. In chromosomes 3p, 3q, and 12q, a significant gain was detected in at least two of the samples, and in 16p, in one sample. In chromosomes 4q and 12q, where also downward expression bias was identified, a loss was detected by CGH in one and two of the samples, respectively (FIG. 4C).

Example 4

A Subset of Genes was Found to Change Following Therapy (Example of One Patient)

Figure 5B:
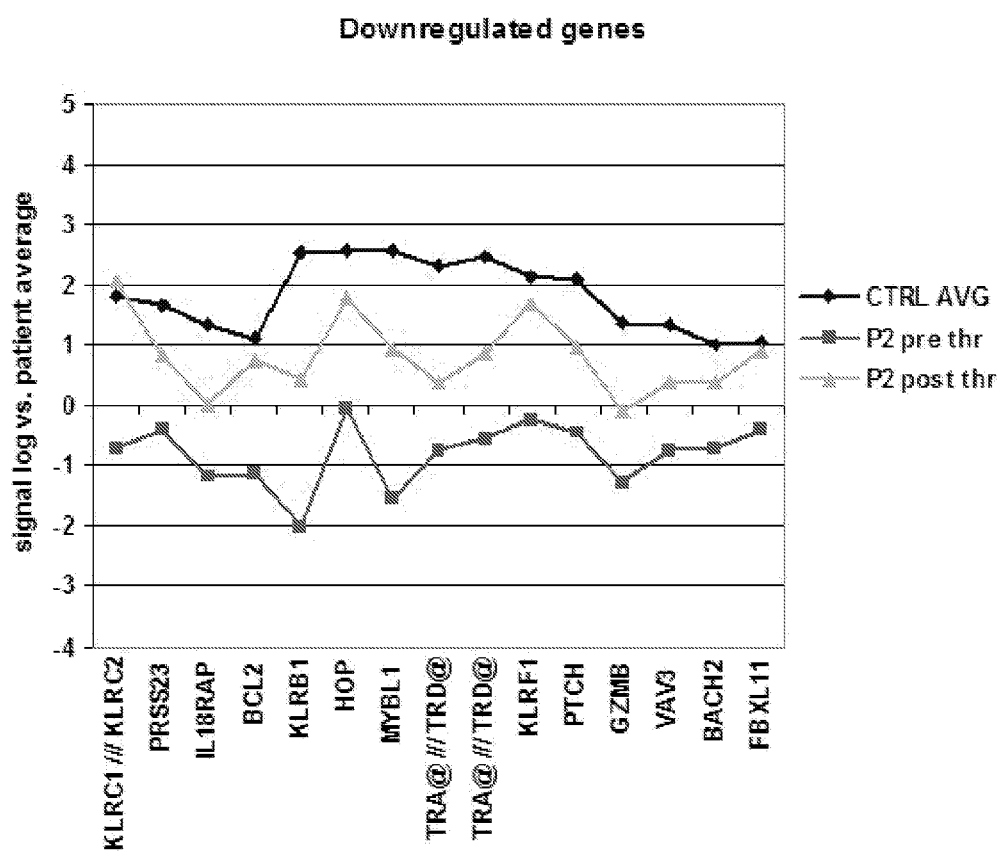
FIG. 5 shows that the gene expression profile reflected the size of tumor burden in an SzS patient. The gene expression profile of patient P2 (Table 1) was analyzed before (pre thr) and after (post thr) cancer therapy. Among the probe sets differentially regulated in SzS and control PBMC samples, a group of probe sets changed over 2-fold towards the control phenotype as a consequence of successful treatment. The upregulated (A) and down-regulated (B) probe sets are presented as compared to the average expression of these probe sets in all patient samples. The changes in gene expression correlated with the clinical phenotype of the patient before (C) and after (D) treatment. The percentage of Sezary cells of blood lymphocytes is indicated in the inserts.
Figure 5C:
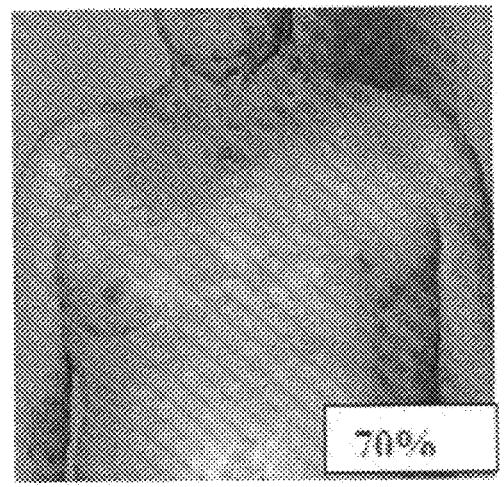
Figure 5D:
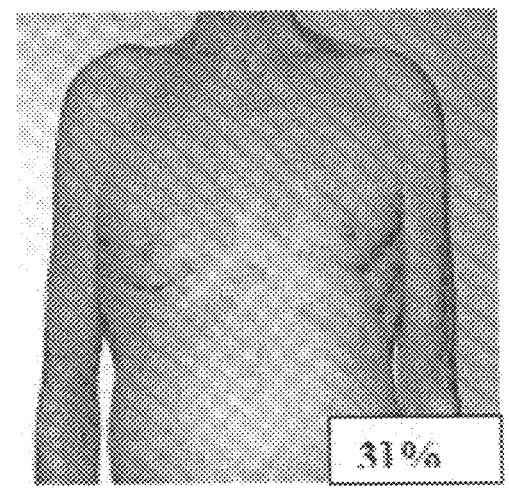
Figure 6A:
FIGS. 6A-D show immunohistochemical detection of CD52 and IL7R, found upregulated at RNA level, in lesional mycosis fungoides and Sezary syndrome skin samples before therapy. A) Abundant expression of CD52 protein in the skin-infiltrating lymphocytes of CTCL (Patient P2). Magnification, ×15. B) Only few CD52+ lymphocytes were found in inflammatory lesions (case C14). Magnification, ×40. C) IL7R is expressed by ~30% of lesional lymphocytes in CTCL (patient P15). Magnification, ×60. D) Only few cells are positive for IL7R in the inflammatory control samples.
Figure 6B:
Figure 6C:
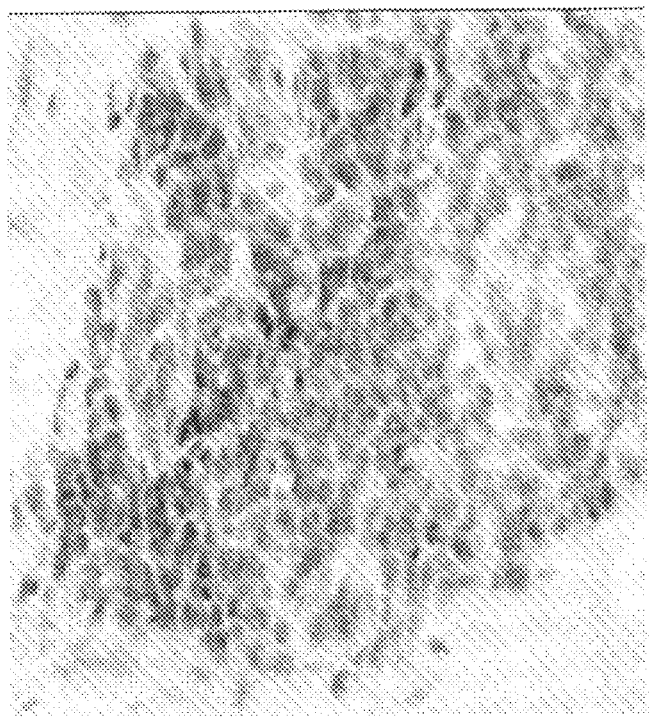
Figure 6D:
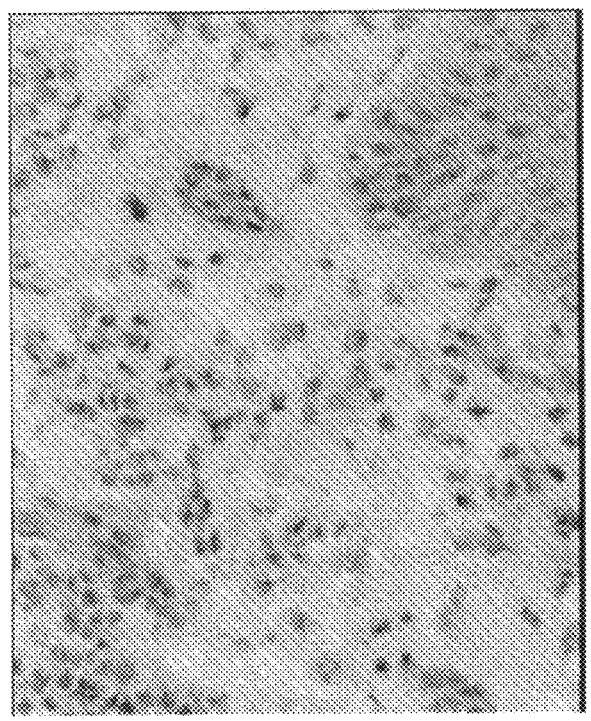

A follow-up PBMC sample of one of the Sezary syndrome patients (case 2, described in Example 1a, Table 1) was obtained 19 months after a continuous therapy resulting in clinical response. Among the probe sets differentially regulated in SzS PBMC samples, when compared to control PBMC samples, a group of 57 probe sets was changed towards the control phenotype after successful therapy (FIG. 5). The therapy-responsive genes included e.g. S100P, CCR10, BCL2, VAV3 and GZMB.

TABLE 1

Characteristics of patient and reference samples included into the study

| | Sex and Age | Diagnosis | Array | QPCR | IHC | Chromosomal clone* | Prior therapy | SzS | Other |
|---|---|---|---|---|---|---|---|---|---|
| Patients | | | | | | | | | |
| P1 § | M52 | SzS | PBMC | PBMC | skin | t(1; 5), del (9) | nil | 40% | DOD |
| P2 § | M63 | SzS | PBMC | PBMC | skin | t(2; 5) | nil | 70% | |
| | M65 | SzS, follow-up sample | PBMC, CD4+ | | | t(2; 5) | C + P, B | 31% | |
| P3 § | M72 | SzS | PBMC | PBMC | | none | nil | 16% | DOD |
| P4 | M72 | SzS | PBMC | PBMC | | | nil | 33% | |
| P5 ‖ | M58 | MF IB | PBMC, CD4+, skin | PBMC, CD4+, skin | skin | del (12q21-22) †, NAV3 deletion ‡ | nil | | |
| P6 | F69 | MFIB | PBMC | PBMC | | | PUVA, chemotherapy | | DOD |
| P7 ‖ | M71 | MF IB, CD30+ | PBMC, CD4+, skin | PBMC, CD4+ | skin | NAV3 deletion ‡ | PUVA | | |
| P8 ‖ | F79 | MF IA | PBMC, CD4+, skin | PBMC, CD4+, skin | | none | nil | | |
| P9 | F45 | MF IVB | PBMC | PBMC | | | PUVA, UVB, retinoids | | |
| P10 | F73 | MF | | skin | | ND | PUVA | | |
| P11 (MF1) | F59 | MF | | PBMC | | ND | electron beam | | |
| P12 (SzS1) | M58 | SzS | | PBMC | | ND | nil | | |
| P13 (SzS2) | M74 | SzS | | PBMC | | ND | methotrexate | | |
| P14 | M62 | MF | | | skin | NAV3 deletion ‡ | | | |
| P15 | M76 | MF | | | skin | NAV3 deletion ‡ | | | |
| P16 | F56 | MF | | | skin | NAV3 deletion ‡ | | | |
| P17 | M42 | MF | | | skin | NAV3 deletion ‡ | | | |
| P18 | M55 | MF | | | skin | NAV3 deletion ‡ | | | |
| P19 | M58 | SzS | | | skin | | | | |
| P20 | M62 | SzS | | | skin | | | | |
| Controls | | | | | | | | | |
| C1 | M27 | Control | PBMC, CD4+ | PBMC, CD4+ | | | | | |
| C2 | M49 | Control | PBMC, CD4+ | PBMC, CD4+ | | | | | |
| C3 | F52 | Control | PBMC, CD4+ | PBMC, CD4+ | | | | | |
| C4 | M67 | Control | PBMC, CD4+ | PBMC, CD4+ | | | | | |
| C5 | F66 | Control | PBMC, CD4+ | PBMC, CD4+ | | | | | |
| C6 | F51 | Infiltr. lymphocytica | skin | skin | | | | | |
| C7 | F68 | Lichen planus | skin | skin | | | | | |
| C8 | M77 | Eczema | skin | skin | | | | | |
| C9 | F63 | Eczema | skin | skin | | | | | |
| C10 | F72 | Lichen planus | | | skin | | | | |
| C11 | M62 | Lichen planus | | | skin | | | | |
| C12 | F74 | Lichen planus | | | skin | | | | |
| C13 | F76 | Lichen planus | | | skin | | | | |

TABLE 1-continued

Characteristics of patient and reference samples included into the study

| | Sex and Age | Diagnosis | Array | QPCR | IHC | Chromosomal clone* | Prior therapy | SzS | Other |
|---|---|---|---|---|---|---|---|---|---|
| C14 | M59 | Eczema | | | skin | | | | |
| C15 | F69 | Eczema | | | skin | | | | |

Array = samples studied with Affymetrix microarray
QPCR = samples studied with real-time quantitative PCR
IHC = samples studied immunohistologically
SzS = percentage of morphological Sezary cells of lymphocytes
*detected with MFISH
† detected with G-banding or
‡ FISH as described in Karenko et al. 2005
§ CGH from PBMC
|| CGH from lesional skin
C + P = chlorambusil + prednison, B = bexarotene, PUVA = psoralen + UVA photochemotherapy
DOD = died of disease
ND = not done

TABLE 2

Genes showing similar expression profiles in all CTCL subtypes and in different tissue samples (fold change of at least 2, p-value less than 0.05)

| Gene | GO* | Probe ID | UniGene ID | Locus |
|---|---|---|---|---|
| ZBTB16 | nucleid acid binding | 205883_at | Hs.171299 | 11q23.1 |
| CD160 | receptor activity | 207840_at | Hs.488237 | 1q21.1 |
| HIST2H2AA | — | 218280_x_at | Hs.530461 | 1q21.2 |
| HIST2H2AA | — | 214290_s_at | Hs.530461 | 1q21.2 |
| HBD | oxygen transporter activity | 206834_at | Hs.36977 | 11p15.5 |
| MMP9 | gelatinase B actvity | 203936_s_at | Hs.297413 | 20q11.2-q13.1 |
| SNCA | protein binding | 204466_s_at | Hs.271771 | 4q21 |
| YWHAE | protein domain specific binding | 213655_at | Hs.513851 | 17p13.3 |
| LIR9 | — | 215838_at | Hs.512233 | 19q13.4 |
| TOP1 | DNA topoisomerase type I activity | 208900_s_at | Hs.472737 | 20q12-q13.1 |
| S100P | calcium ion binding | 204351_at | Hs.2962 | 4p16 |
| STAT1 | trancription factor activity | 209969_s_at | Hs.470943 | 2q32.2 |
| TRIB1 | protein kinase activity | 202241_at | Hs.444947 | 8q24.13 |
| GLIPR1 | — | 204221_x_at | Hs.553516 | 12q21.1 |
| GLIPR1 | — | 214085_x_at | Hs.553516 | 12q21.1 |
| GLUL | glutamate-ammonia ligase activity | 217202_s_at | Hs.518525 | 1q31 |
| MS4A4A | receptor activity | 219607_s_at | Hs.325960 | 11q12 |
| PSMB3 | threonine endopeptidase activity | 201400_at | Hs.82793 | 17q12 |
| ITM2A | — | 202747_s_at | Hs.17109 | Xq13.3-Xq21.2 |
| ETHE1 | — | 204034_at | Hs.7486 | 19q13.31 |
| BARD1 | ubiquitin-protein ligase activity | 205345_at | Hs.54089 | 2q34-q35 |
| RECQL | nucleotide binding | 212918_at | Hs.235069 | 12p12 |
| HIST2H2BE | DNA binding | 202708_s_at | Hs.2178 | 1q21-q23 |
| CDC42 | nucleotide binding | 208727_s_at | Hs.467637 | 1p36.1 |
| RPL31 | structural constituent of ribosome | 200962_at | Hs.469473 | 2q11.2 |
| LOC55831 | — | 217882_at | Hs.475392 | 3p25.3 |
| G0S2 | — | 213524_s_at | Hs.432132 | 1q32.2-q41 |
| ARPC1A | — | 200950_at | Hs.124126 | 7q22.1 |
| C1QBP | — | 208910_s_at | Hs.553487 | 17p13.3 |
| C1QBP | — | 214214_s_at | Hs.553487 | 17p13.3 |

| | SzS PBMC | | MF PBMC | | MF CD4+ | | MF Skin | |
|---|---|---|---|---|---|---|---|---|
| Gene | M | P | M | P | M | P | M | P |
| ZBTB16 | −1.84 | 0.0001 | −1.07 | 0.0014 | — | — | — | — |
| CD160 | −3.51 | 0.0000 | −1.64 | 0.0290 | — | — | — | — |
| HIST2H2AA | 1.32 | 0.0021 | 1.43 | 0.0063 | 2.09 | 0.0180 | — | — |
| HIST2H2AA | 1.39 | 0.0008 | 1.19 | 0.0250 | 2.36 | 0.0220 | — | — |
| HBD | 3.45 | 0.0057 | 1.86 | 0.0065 | — | — | — | — |
| MMP9 | 1.98 | 0.0083 | 1.17 | 0.0070 | — | — | — | — |
| SNCA | 2.08 | 0.0120 | 1.48 | 0.0079 | † | † | 1.19 | 0.0250 |
| YWHAE | 1.25 | 0.0033 | 1.06 | 0.0340 | — | — | — | — |
| LIR9 | 1.10 | 0.0065 | 1.09 | 0.0360 | 1.91 | 0.0001 | — | — |
| TOP1 | 1.18 | 0.0026 | 1.29 | 0.0480 | — | — | ‡ | ‡ |
| S100P | 2.21 | 0.0230 | 2.12 | 0.0220 | — | — | — | — |
| STAT1 | 1.24 | 0.0270 | 1.10 | 0.0410 | — | — | — | — |
| TRIB1 | 1.07 | 0.0390 | — | — | 3.36 | 0.0240 | — | — |
| GLIPR1 | 1.14 | 0.0180 | — | — | 1.01 | 0.0083 | — | — |
| GLIPR1 | 1.20 | 0.0270 | — | — | 1.05 | 0.0090 | — | — |

TABLE 2-continued

Genes showing similar expression profiles in all CTCL subtypes and in different tissue samples (fold change of at least 2, p-value less than 0.05)

| | | | | | | | |
|---|---|---|---|---|---|---|---|
| GLUL | 1.54 | 0.0078 | — | — | 1.57 | 0.0260 | — | — |
| MS4A4A | 1.96 | 0.0140 | — | — | 1.52 | 0.0370 | — | — |
| PSMB3 | 1.15 | 0.0059 | — | — | — | — | 1.26 | 0.0047 |
| ITM2A | 1.17 | 0.0350 | — | — | — | — | 1.75 | 0.0200 |
| ETHE1 | 1.29 | 0.0260 | — | — | — | — | 1.40 | 0.0340 |
| BARD1 | 1.03 | 0.0220 | — | — | — | — | 1.28 | 0.0320 |
| RECQL | 1.06 | 0.0085 | — | — | — | — | 1.00 | 0.0440 |
| HIST2H2BE | — | — | 1.73 | 0.0270 | 2.46 | 0.0490 | — | — |
| CDC42 | — | — | −1.00 | 0.0058 | −1.36 | 0.0220 | † | † |
| RPL31 | — | — | −1.14 | 0.0470 | −2.27 | 0.0008 | — | — |
| LOC55831 | — | — | 1.06 | 0.0091 | 1.13 | 0.0440 | — | — |
| G0S2 | — | — | 1.55 | 0.0360 | 3.73 | 0.0200 | — | — |
| ARPC1A | — | — | — | — | 1.06 | 0.0230 | 1.28 | 0.0072 |
| C1QBP | — | — | — | — | −1.39 | 0.0008 | −1.20 | 0.0420 |
| C1QBP | — | — | — | — | −1.22 | 0.0012 | −1.30 | 0.0110 |

*GO Molecular function
† Statistically significant change to the same direction
‡ Statistically significant change to the opposite direction

TABLE 3

Genes found to be differentially expressed and relevant to CTCL pathogenesis.

| Gene designation | Finding | Molecular function | Presumed function or expected functional consequence |
|---|---|---|---|
| TBX21 (T-bet) | Downregulated | Transcription factor | Th1 down |
| SCYA5 (Rantes) | Downregulated | Chemokine | Th1 down |
| NKG7 | Downregulated | Th differentiation | Th1 down |
| XCL1 (lymphotactin) | Downregulated | Chemokine, T-cell cytotoxicity (CTL) | Th1 down, lack of CTL activity |
| TXK | Downregulated | Transcription factor | Th1 down |
| GZMB (granzymeB) | Downregulated | T-cell cytotoxicity | Th1 down, lack of CTL activity |
| S100P | Upregulated | Th2 polarisation, cell cycle and differentition | Th2 up |
| LIR9 | Upregulated | Membrane receptor, induces IL-1β, TNF-α and IL-6 | Th2 up |
| KIR3DL2 | Downregulated | Membrane receptor | Lack of CTL activity |
| IL2Rβ | Downregulated | Cytokine receptor | Impaired immune response |
| VAV3 | Downregulated | Signal transduction, activates e.g. Rho family | Disturbed T cell activation |
| DLG5 | Downregulated | Tumor suppressor | Increases cell proliferation |
| MMP-9 | Upregulated | Matrix metalloproteinase | Carcinogenesis and tumour spread |
| IL7R | Upregulated (basal keratinocytes) | Cytokine receptor | Lymphocyte activation and homing to epidermis |
| CD52 | Upregulated | Membrane antigen | (target molecule of alemtuzumab) |
| MS4A4A | Upregulated | Membrane antigen | Signal transduction in haematopoietic cells |

TABLE 4

Real-time RT-PCR reagents

| Probe ID | Target gene | 1) 5'-F primer-3'<br>2) 5'-R primer-3'<br>3) 5'-Probe-3' | Sequence identifier |
|---|---|---|---|
| 201681_s_at | DLG5 | 1) GGGGTAGGGGCTGTTTTCTA<br>2) TGTGCACACTGTACCATCTCAG<br>3) Probelibrary Human#13 | SEQ ID NO: 1<br>SEQ ID NO: 2 |
| | EF1a | 1) CTGAACCATCCAGGCCAAAT<br>2) GCCGTGTGGCAATCCAAT<br>3) AGCGCCGGCTATGCCCCTG | SEQ ID NO: 3<br>SEQ ID NO: 4<br>SEQ ID NO: 5 |

TABLE 4-continued

Real-time RT-PCR reagents

| Probe ID | Target gene | 1) 5'-F primer-3'<br>2) 5'-R primer-3'<br>3) 5'-Probe-3' | Sequence identifier |
|---|---|---|---|
| 205291_at | IL2Rb | 1) CCCAATACAAAAATACCTACTGCTG<br>2) TTTGGATATAAAGGCAACAGGAA<br>3) Probelibrary Human#66 | SEQ ID NO: 6<br>SEQ ID NO: 7 |
| 207314_x_at | KIR3DL2_1 | 1) CTGAGCCCAGATCCAAAGTT<br>2) AACCCCCTCAAGACCTGACT<br>3) Probelibrary Human#51 | SEQ ID NO: 8<br>SEQ ID NO: 9 |
|  | KIR3DL2_2 | 1) CAGTGACGCCCTGGACAT<br>2) GAGCTACAGGACAAGGTCACG<br>3) Probelibrary Human#51 | SEQ ID NO: 10<br>SEQ ID NO: 11 |
| 215838_at | LIR9 | 1) TCCTGCAGGTATGGTCAGAA<br>2) ACTGAGGTTATCAGCTGCTCCT<br>3) Probelibrary Human#79 | SEQ ID NO: 12<br>SEQ ID NO: 13 |
| 203936_s_at | MMP9 | 1) GTGCCATGTAAATCCCCACT<br>2) TTTGTATCCGGCAAACTGG<br>3) Probelibrary Human#60 | SEQ ID NO: 14<br>SEQ ID NO: 15 |
| 213915_at | NKG7 | 1) TCCCTGGGCCTGATGTTCT<br>2) TGGGACCCACAGCCTCAA<br>3) CCTGATTGCTTTGAGCACCGATTTCTG | SEQ ID NO: 16<br>SEQ ID NO: 17<br>SEQ ID NO: 18 |
| 204351_at | S100P | 1) CATTTGAGTCCTGCCTTCTCAAA<br>2) CCGTGGATAAATTGCTCAAGGA<br>3) CATTTGAGTCCTGCCTTCTCAAA | SEQ ID NO: 19<br>SEQ ID NO: 20<br>SEQ ID NO: 21 |
| 203408_s_at | SATB1 | 1) CCGTAAGCATGAAACCAGTG<br>2) GATCAGTGTGGAGTGCTACAGAA<br>3) Probelibrary Human#55 | SEQ ID NO: 22<br>SEQ ID NO: 23 |
| 204655_at | SCYA5 | 1) TCCCGAACCCATTTCTTCTCT<br>2) CCCAGCAGTCGTCTTTGTCA<br>3) TTGGCACACACTTGGCGGTTCTTTC | SEQ ID NO: 24<br>SEQ ID NO: 25<br>SEQ ID NO: 26 |
| 204466_s_at | SNCA | 1) TGTTCCATCCTGTACAAGTGCT<br>2) CGAGATACACTGTAAAAACTTTGAGAA<br>3) Probelibrary Mouse#80 | SEQ ID NO: 27<br>SEQ ID NO: 28 |
| 220684_at | TBX21 | 1) ACAGCTATGAGGCTGAGTTTCGA<br>2) GGCCTCGGTAGTAGGACATGGT<br>3) TCAGCATGAAGCCTGCATTGTTGCC | SEQ ID NO: 29<br>SEQ ID NO: 30<br>SEQ ID NO: 31 |
| 218807_at | VAV3 | 1) CGTCAGCCGAACTTTGTTATG<br>2) TCCACAGGAGTGTTTCTGCTT<br>3) Probelibrary Human#80 | SEQ ID NO: 32<br>SEQ ID NO: 33 |

---

The invention claimed is:

1. A method for detecting cutaneous T-cell lymphoma (CTCL) in a human subject, said method comprising:
   measuring a first expression level of MS4A4A mRNA in a peripheral blood mononuclear cell (PBMC) sample taken from the human subject; and
   comparing the first expression level of MS4A4A mRNA to an expression level of MS4A4A mRNA in PBMC samples from a control population of human subjects without CTCL;
   wherein the first expression level of MS4A4A mRNA is statistically significantly greater than the expression level of MS4A4A mRNA in PBMC samples from a control population, and the statistically significantly greater expression of MS4A4A mRNA in the PBMC sample taken from the human subject is indicative of the presence of CTCL in the human subject.

2. The method of claim 1 further comprising measuring expression of mRNA of at least one gene selected from the group consisting of: ZBTB16, CD160, HIST2H2AA, HBD, MMP9, SNCA, YWHAE, LIR9, TOP1, S100P, STAT1, TRIB1, GLIPR1, GLUL, PSMB3, ITM2A, ETHE1, BARD1, RECQL, HIST2, H2BE, CDC42, RPL31, LOC55831, G0S2, ARPC1A, C1QBP, TBX21 (T-bet), SCYA5 (Rantes), NKG7, XCL1 (lymphotactin), TXK, GZMB (granzymeB), KIR3DL2, IL2Rβ, VAV3, DLG5, IL7R, and CD52.

3. The method of claim 1 wherein the subject has been treated with a CTCL therapy.

4. The method of claim 1 wherein said CTCL is a CTCL subtype selected from the group consisting of: mycosis fungoides (MF) or Sezary syndrome (SzS).

5. The method of claim 1 further comprising detecting underexpression or overexpression of one or several genes characteristic of Th1 or Th2 polarization.

6. The method of claim 2, wherein overexpression of LIR9 is characteristic of Th2 polarization.

7. The method of claim 2, characterized in that wherein underexpression of NKG7, TBX21 or SCYA5 is characteristic of Th2 polarization.

8. The method of claim 1 wherein an early stage of CTCL is detected.

9. The method of claim 1 wherein a late stage of CTCL is detected.

* * * * *

SEQUENCE LISTING

<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ggggtagggg ctgttttcta                    20

<210> SEQ ID NO 2
<211> LENGTH: 22
<212> TYPE: DNA
<213> ORGANISM: Artificial Sequence

```
<220> FEATURE:
<223> OTHER INFORMATION: Primer

<400> SEQUENCE: 2
tgtgcacact gtaccatctc ag                                              22

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ctgaaccatc caggccaaat                                                 20

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
gccgtgtggc aatccaat                                                   18

<210> SEQ ID NO 5
<211> LENGTH: 19
<212> TYPE: DNA
<213> ORGANISM: Artificial Sequence
<220> FEATURE:
<223> OTHER INFORMATION: Probe

<400> SEQUENCE: 5
agcgccggct atgcccctg                                                  19

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
cccaatacaa aaatacctac tgctg                                           25

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
tttggatata aaggcaacag gaa                                             23

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ctgagcccag atccaaagtt                                                 20
```

```
<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9 aacccccctca agacctgact                                              20

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
cagtgacccc ctggacat                                                 18

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gagctacagg acaaggtcac g                                             21

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tcctgcaggt atggtcagaa                                               20

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
actgaggtta tcagctgctc ct                                            22

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gtgccatgta aatccccact                                               20

<210> SEQ ID NO 15
<211> LENGTH: 19
<212> TYPE: DNA
<213> ORGANISM: Artificial Sequence
<220> FEATURE:
<223> OTHER INFORMATION: Primer
```

-continued

```
<400> SEQUENCE: 15
tttgtatccg gcaaactgg                                                    19

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
tccctgggcc tgatgttct                                                    19

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
tgggacccac agcctcaa                                                     18

<210> SEQ ID NO 18
<211> LENGTH: 27
<212> TYPE: DNA
<213> ORGANISM: Artificial Sequence
<220> FEATURE:
<223> OTHER INFORMATION: Probe

<400> SEQUENCE: 18
cctgattgct ttgagcaccg atttctg                                           27

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
catttgagtc ctgccttctc aaa                                               23

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
ccgtggataa attgctcaag ga                                                22

<210> SEQ ID NO 21
<211> LENGTH: 23
<212> TYPE: DNA
<213> ORGANISM: Artificial Sequence
<220> FEATURE:
<223> OTHER INFORMATION: Probe

<400> SEQUENCE: 21
catttgagtc ctgccttctc aaa                                               23
```

```
<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ccgtaagcat gaaaccagtg                                               20

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
gatcagtgtg gagtgctaca gaa                                           23

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
tcccgaaccc atttcttctc t                                             21

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cccagcagtc gtctttgtca                                               20

<210> SEQ ID NO 26
<211> LENGTH: 25
<212> TYPE: DNA
<213> ORGANISM: Artificial Sequence
<220> FEATURE:
<223> OTHER INFORMATION: Probe

<400> SEQUENCE: 26
ttggcacaca cttggcggtt ctttc                                         25

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
tgttccatcc tgtacaagtg ct                                            22

<210> SEQ ID NO 28
<211> LENGTH: 27
<212> TYPE: DNA
<213> ORGANISM: Artificial Sequence
<220> FEATURE:
<223> OTHER INFORMATION: Primer
```

```
<400> SEQUENCE: 28
cgagatacac tgtaaaaact ttgagaa                                          27

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
acagctatga ggctgagttt cga                                              23

<210> SEQ ID NO 30
<211> LENGTH: 22
<212> TYPE: DNA
<213> ORGANISM: Artificial Sequence
<220> FEATURE:
<223> OTHER INFORMATION: Primer

<400> SEQUENCE: 30
ggcctcggta gtaggacatg gt                                               22

<210> SEQ ID NO 31
<211> LENGTH: 25
<212> TYPE: DNA
<213> ORGANISM: Artificial Sequence
<220> FEATURE:
<223> OTHER INFORMATION: Probe

<400> SEQUENCE: 31
tcagcatgaa gcctgcattc ttgcc                                            25

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
cgtcagccga actttgttat g                                                21

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
tccacaggag tgtttctgct t                                                21
```